US012099050B2

United States Patent
Lloyd et al.

(10) Patent No.: US 12,099,050 B2
(45) Date of Patent: Sep. 24, 2024

(54) METHOD AND SYSTEM FOR PARTIALLY OR FULLY AUTOMATED BUOYANCY-ASSISTED SEPARATION

(71) Applicant: Akadeum Life Sciences, Inc., Ann Arbor, MI (US)

(72) Inventors: William Lloyd, Ann Arbor, MI (US); Brittany MacIntyre, Ann Arbor, MI (US); Maureen Carey, Ann Arbor, MI (US); Casey Wegner, Ann Arbor, MI (US); Brandon H. McNaughton, Ann Arbor, MI (US)

(73) Assignee: Akadeum Life Sciences, Inc., Ann Arbor, MI (US)

( * ) Notice: Subject to any disclaimer, the term of this patent is extended or adjusted under 35 U.S.C. 154(b) by 0 days.

(21) Appl. No.: 18/441,894

(22) Filed: Feb. 14, 2024

(65) Prior Publication Data
US 2024/0272139 A1     Aug. 15, 2024

Related U.S. Application Data

(60) Provisional application No. 63/445,391, filed on Feb. 14, 2023.

(51) Int. Cl.
*G01N 33/49*     (2006.01)
*G01N 35/00*     (2006.01)
*G01N 35/10*     (2006.01)

(52) U.S. Cl.
CPC ....... *G01N 33/491* (2013.01); *G01N 35/1097* (2013.01); *G01N 2035/00465* (2013.01)

(58) Field of Classification Search
CPC ............. G01N 33/491; G01N 35/1097; G01N 2035/00465
See application file for complete search history.

(56) References Cited

U.S. PATENT DOCUMENTS 3,381,283 A    4/1968   Gyorgy et al.
3,586,064 A    6/1971   Brown et al.
(Continued)

FOREIGN PATENT DOCUMENTS

DE    3381283        4/1990
EP    0778944 B1    11/1999
(Continued)

OTHER PUBLICATIONS

Corrosionpedia—Diaphragm Pump—Published: Oct. 2, 2014 Updated: May 4, 2019 (Year: 2019).
(Continued)

*Primary Examiner* — Benjamin L Lebron
(74) *Attorney, Agent, or Firm* — Jeffrey Schox; Annie Imbrie-Moore

(57) ABSTRACT

A system for partially or fully automated, buoyancy-assisted separation includes and/or interfaces with an automated instrument. Additionally or alternatively, the system can include and/or interface with any or all of: a set of buoyant particles, a set of containers (individually and/or collectively equivalently referred to herein as a consumable), a $1^{st}$ container management subsystem, a $2^{nd}$ container management subsystem, a user interface subsystem, and/or any other components. A method for partially or fully automated, buoyancy-assisted separation includes manipulating the set of containers and/or processing the set of materials at a $1^{st}$ container management subsystem; and manipulating the set of containers and/or processing the set of materials at a $2^{nd}$ container management subsystem.

20 Claims, 33 Drawing Sheets

(56) References Cited

U.S. PATENT DOCUMENTS

| | | |
|---|---|---|
| 3,692,493 A | 9/1972 | Terasaki |
| 3,920,549 A | 11/1975 | Gigliello et al. |
| 4,086,060 A | 4/1978 | Hermann |
| 4,464,254 A | 8/1984 | Dojki et al. |
| 4,487,700 A | 12/1984 | Kanter |
| 4,689,151 A | 8/1987 | Kosikowski et al. |
| 4,714,680 A | 12/1987 | Civin |
| 4,845,025 A | 7/1989 | Lary et al. |
| 5,116,724 A | 5/1992 | Delaage et al. |
| 5,182,192 A | 1/1993 | Steplewski et al. |
| 5,246,829 A | 9/1993 | Delaage et al. |
| 5,266,199 A | 11/1993 | Tsukagoshi et al. |
| 5,339,830 A | 8/1994 | Blake |
| 5,354,483 A | 10/1994 | Furse |
| 5,594,164 A | 1/1997 | Bull |
| 5,639,382 A | 6/1997 | Brown |
| 5,674,173 A | 10/1997 | Hlavinka et al. |
| 5,730,864 A | 3/1998 | Delsalle et al. |
| 5,853,600 A | 12/1998 | Mcneal et al. |
| 5,874,266 A | 2/1999 | Palsson |
| 6,036,940 A | 3/2000 | Ju et al. |
| 6,151,113 A | 11/2000 | Odonohue et al. |
| 6,221,315 B1 | 4/2001 | Giesler et al. |
| 6,261,537 B1 | 7/2001 | Klaveness et al. |
| 6,264,917 B1 | 7/2001 | Klaveness et al. |
| 6,331,289 B1 | 12/2001 | Klaveness et al. |
| 6,416,739 B1 | 7/2002 | Rogerson et al. |
| 6,506,167 B1 | 1/2003 | Ishimoto et al. |
| 6,528,039 B2 | 3/2003 | Unger |
| 6,544,424 B1 | 4/2003 | Shevitz |
| 6,569,340 B2 | 5/2003 | Kopf |
| 6,652,136 B2 | 11/2003 | Marziali |
| 6,723,303 B1 | 4/2004 | Quay |
| 6,919,031 B2 | 7/2005 | Blumenschein et al. |
| 7,524,641 B2 | 4/2009 | Jurgensen et al. |
| 7,704,393 B2 | 4/2010 | Noh et al. |
| 7,736,593 B2 | 6/2010 | Dastane et al. |
| 7,771,590 B2 | 8/2010 | Leach et al. |
| 7,915,540 B2 | 3/2011 | Oggioni |
| 7,947,236 B2 | 5/2011 | Losada et al. |
| 7,981,286 B2 | 7/2011 | Higuchi et al. |
| 8,048,320 B2 | 11/2011 | Leach et al. |
| 8,066,127 B2 | 11/2011 | Coelho et al. |
| 8,177,072 B2 | 5/2012 | Chapman et al. |
| 8,183,039 B2 | 5/2012 | Schmitz et al. |
| 8,290,714 B2 | 10/2012 | Ignatius et al. |
| 8,513,032 B2 | 8/2013 | Jablonski et al. |
| 8,540,082 B2 | 9/2013 | Kelland et al. |
| 8,617,884 B2 | 12/2013 | Berenson et al. |
| 8,747,289 B2 | 6/2014 | Coelho |
| 8,834,698 B2 | 9/2014 | Lau et al. |
| 8,835,186 B2 | 9/2014 | Jablonski et al. |
| 9,011,819 B2 | 4/2015 | Rychak |
| 9,039,999 B2 | 5/2015 | Campton et al. |
| 9,114,334 B2 | 8/2015 | Leach et al. |
| 9,119,508 B2 | 9/2015 | Reed |
| 9,120,095 B2 | 9/2015 | OConnell |
| 9,234,890 B2 | 1/2016 | Adams et al. |
| 9,410,182 B2 | 8/2016 | Wu |
| 9,410,183 B2 | 8/2016 | Wu |
| 9,435,799 B2 | 9/2016 | Russell et al. |
| 9,506,930 B2 | 11/2016 | Ignatius et al. |
| 9,528,088 B2 | 12/2016 | Berenson et al. |
| 9,551,706 B2 | 1/2017 | Phillips et al. |
| 9,599,545 B2 | 3/2017 | Coelho |
| 9,695,394 B1 | 7/2017 | Coelho et al. |
| 9,766,237 B2 | 9/2017 | Jablonski et al. |
| 9,790,467 B2 | 10/2017 | Kevlahan et al. |
| 9,797,817 B2 | 10/2017 | Mcnaughton et al. |
| 9,821,111 B2 | 11/2017 | Coelho et al. |
| 9,841,360 B1 | 12/2017 | Solazzi |
| 9,857,361 B2 | 1/2018 | Wanders et al. |
| 10,052,427 B2 | 8/2018 | Flieg et al. |
| 10,132,309 B2 | 11/2018 | Manzarek et al. |
| 10,195,280 B2 | 2/2019 | De Mollerat Du Jeu et al. |
| 10,195,547 B2 | 2/2019 | Mcnaughton et al. |
| 10,273,504 B2 | 4/2019 | Miltenyi et al. |
| 10,302,536 B2 | 5/2019 | Shi et al. |
| 10,407,486 B2 | 9/2019 | Schmitz et al. |
| 10,479,976 B2 | 11/2019 | Shi et al. |
| 10,585,088 B2 | 3/2020 | Gohel et al. |
| 10,640,275 B2 | 5/2020 | Mcgrath et al. |
| 10,640,276 B2 | 5/2020 | Mcgrath et al. |
| 10,684,172 B2 | 6/2020 | Carron et al. |
| 10,739,338 B2 | 8/2020 | Kevlahan et al. |
| 10,752,689 B2 | 8/2020 | Aggeler et al. |
| 10,792,362 B2 | 10/2020 | De Mollerat Du Jeu et al. |
| 10,794,900 B2 | 10/2020 | Wanders et al. |
| 10,859,477 B2 | 12/2020 | Nakamura et al. |
| 10,890,586 B2 | 1/2021 | Wu et al. |
| 10,934,519 B2 | 3/2021 | Roy et al. |
| 11,007,285 B2 | 5/2021 | Butts et al. |
| 11,046,738 B2 | 6/2021 | Person et al. |
| 11,105,796 B2 | 8/2021 | Fuerstenberg et al. |
| 11,141,435 B2 | 10/2021 | Coelho et al. |
| 11,155,714 B2 | 10/2021 | Xu et al. |
| 11,247,178 B2 | 2/2022 | Smyslova et al. |
| 11,291,931 B2 | 4/2022 | Mcnaughton et al. |
| 11,339,407 B2 | 5/2022 | Waters et al. |
| 11,524,985 B2 | 12/2022 | Kalabokis et al. |
| 11,565,237 B2 | 1/2023 | Kevlahan et al. |
| 11,819,842 B2 | 11/2023 | Wegner et al. |
| 2002/0048819 A1 | 4/2002 | Alley |
| 2003/0066850 A1 | 4/2003 | Young |
| 2003/0104359 A1 | 6/2003 | Cuthbertson et al. |
| 2004/0023222 A1 | 2/2004 | Russell et al. |
| 2004/0166029 A1 | 8/2004 | Losada et al. |
| 2005/0059163 A1 | 3/2005 | Dastane et al. |
| 2006/0054191 A1 | 3/2006 | Higuchi et al. |
| 2006/0131236 A1 | 6/2006 | Belfort et al. |
| 2006/0283896 A1 | 12/2006 | Kasting |
| 2007/0015191 A1 | 1/2007 | Bitner et al. |
| 2007/0036722 A1 | 2/2007 | Rongved et al. |
| 2007/0075016 A1 | 4/2007 | Leach |
| 2007/0190584 A1 | 8/2007 | Jurgensen et al. |
| 2008/0034509 A1 | 2/2008 | Nuennerich et al. |
| 2009/0042284 A1 | 2/2009 | Tachibana et al. |
| 2010/0285606 A1 | 11/2010 | Phillips et al. |
| 2011/0097816 A1 | 4/2011 | Goodwin |
| 2011/0236884 A1 | 9/2011 | Jablonski et al. |
| 2012/0202225 A1 | 8/2012 | Knutson et al. |
| 2013/0029411 A1 | 1/2013 | Roy et al. |
| 2013/0280767 A1 | 10/2013 | Kobayashi et al. |
| 2014/0161688 A1 | 6/2014 | Campton et al. |
| 2014/0277672 A1 | 9/2014 | Manzarek et al. |
| 2015/0011013 A1 | 1/2015 | Campton et al. |
| 2015/0021963 A1 | 1/2015 | Reed |
| 2015/0080204 A1 | 3/2015 | Kassis |
| 2015/0219636 A1 | 8/2015 | Rychak et al. |
| 2015/0260178 A1 | 9/2015 | Giessbach |
| 2015/0320924 A1 | 11/2015 | Flieg et al. |
| 2016/0167061 A1 | 6/2016 | Mcnaughton et al. |
| 2017/0001191 A1 | 1/2017 | Biadillah et al. |
| 2017/0014819 A1 | 1/2017 | U'Ren et al. |
| 2017/0059552 A1 | 3/2017 | Campton et al. |
| 2017/0183619 A1 | 6/2017 | Coelho et al. |
| 2018/0171295 A1 | 6/2018 | Shi et al. |
| 2018/0290077 A1 | 10/2018 | Mcnaughton et al. |
| 2019/0282619 A1 | 9/2019 | Coelho et al. |
| 2020/0009614 A1 | 1/2020 | Mcnaughton et al. |
| 2020/0017830 A1 | 1/2020 | Shi et al. |
| 2020/0072834 A1 | 3/2020 | Busa et al. |
| 2020/0276540 A1 | 9/2020 | Smyslova et al. |
| 2021/0180108 A1 | 6/2021 | Kim et al. |
| 2023/0314428 A1 | 10/2023 | Snow et al. |

FOREIGN PATENT DOCUMENTS

| | | |
|---|---|---|
| EP | 1073716 B1 | 4/2004 |
| EP | 2104488 B1 | 10/2016 |
| GB | 1407267 A | 9/1975 |
| JP | 2001120964 A | 5/2001 |
| JP | 2014521333 A | 8/2014 |
| WO | 2011052927 A2 | 5/2011 |

(56) References Cited

FOREIGN PATENT DOCUMENTS

| | | |
|---|---|---|
| WO | 2012090863 A1 | 7/2012 |
| WO | 2013096157 A1 | 6/2013 |
| WO | 2015133972 A1 | 9/2015 |
| WO | 2017109072 A1 | 6/2017 |
| WO | 2017190117 A1 | 11/2017 |
| WO | 2023028329 A1 | 3/2023 |

OTHER PUBLICATIONS https://en.wikipedia.org/wiki/Diaphragm_pump (Year: 2021).
https://www.yamadapump.com/what-is-a-double-diaphragm-pump/#:-:text=A (Year: 2021).
Mud Sucker Diaphragm Pumps, https://wastecorp.com/ms-faqs (Year: 2021).
Moon, Sang Ho, "Bio-device for extracting hematopoietic stem cells and mesenchymal stem cells in peripheral blood", Translation of WO 2011/052927 A2, 2011, WIPO, p. 1-23 (Year: 2011).
Wang, Meiyao, "Quantifying CD4 receptor protein in two human CD4+ lymphocyte preparations for quantitative flow cytometry", Clinical proteomics, 11 (1), 43. https://doi.org/10.1186/1559-0275-11-43.

Container at t = $t_8$

US 12,099,050 B2

METHOD AND SYSTEM FOR PARTIALLY OR FULLY AUTOMATED BUOYANCY-ASSISTED SEPARATION

CROSS-REFERENCE TO RELATED APPLICATIONS

This application claims the benefit of U.S. Provisional Application No. 63/445,391, filed 14 Feb. 2023, which is incorporated in its entirety by this reference.

TECHNICAL FIELD

This invention relates generally to the biological processing field, and more specifically to a new and useful system and method for partially or fully automated buoyancy-assisted separation in the biological processing field.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
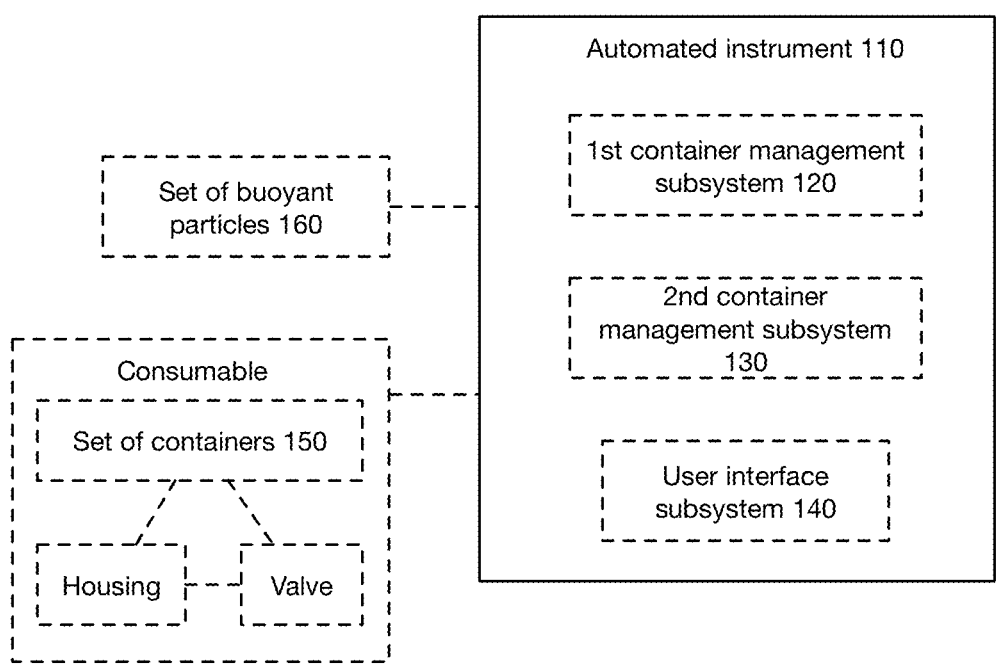
FIG. 1 is a schematic of a system for partially or fully automated buoyancy-assisted separation.

As shown in FIG. 1, a system 100 for partially or fully automated, buoyancy-assisted separation includes and/or interfaces with an automated instrument 110. Additionally or alternatively, the system can include and/or interface with any or all of: a set of buoyant particles 160, a set of containers 150 (individually and/or collectively equivalently referred to herein as a consumable), a $1^{st}$ container management subsystem 120 (equivalently referred to herein as a $1^{st}$ processing subsystem and/or a $1^{st}$ mixing subsystem), a $2^{nd}$ container management subsystem 130 (equivalently referred to herein as a $2^{nd}$ processing subsystem and/or a $2^{nd}$ mixing subsystem), a user interface subsystem 140, and/or any other components. Further additionally or alternatively, the system 100 can include and/or interface with any or all of the components as described in any or all of: U.S. application Ser. No. 16/004,874, filed 11 Jun. 2018, U.S. application Ser. No. 14/969,446, filed 15 Dec. 2015, U.S. application Ser. No. 17/679,688, filed 24 Feb. 2022, and U.S. application Ser. No. 17/896,800, filed 26 Aug. 2022, and U.S. application Ser. No. 18/114,130, filed 24 Feb. 2023, each of which is incorporated in its entirety by this reference.

Figure 2:
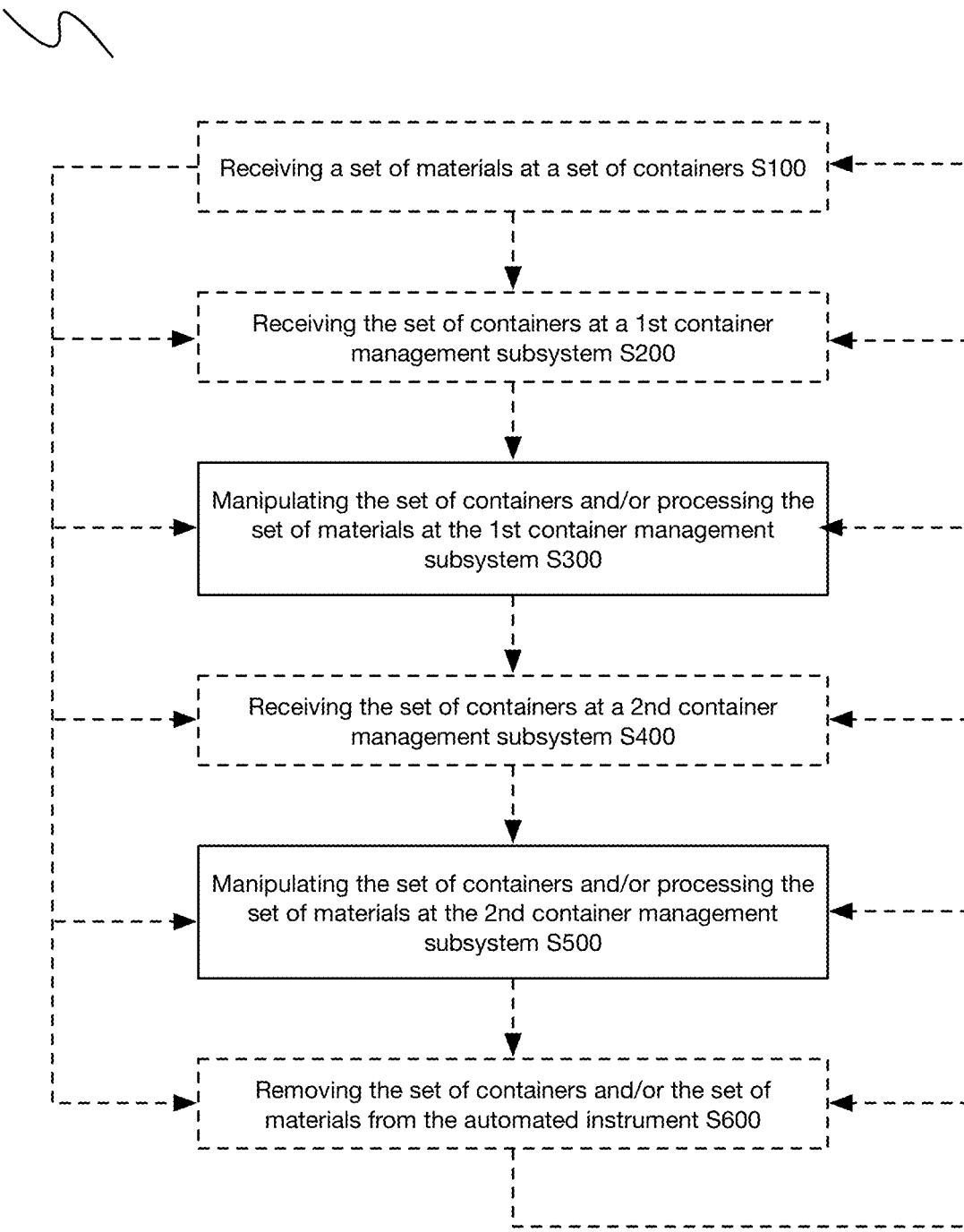
FIG. 2 is a schematic of a method for partially or fully automated buoyancy-assisted separation.

As shown in FIG. 2, a method 200 for partially or fully automated, buoyancy-assisted separation includes manipulating the set of containers and/or processing the set of materials at a $1^{st}$ container management subsystem S300 and manipulating the set of containers and/or processing the set of materials at a $2^{nd}$ container management subsystem S500. Additionally or alternatively, the method 200 can include any or all of: receiving a set of materials at a set of containers S100; receiving the set of containers at a $1^{st}$ container management subsystem S200; receiving the set of containers at a $2^{nd}$ container management subsystem S400; removing the set of containers and/or the set of materials from the automated instrument S600; receiving the set of containers at any other container management subsystems; separating and/or combining containers; and/or any other suitable processes.

Further additionally or alternatively, the method can include and/or interface with any or all of the processes as described in: U.S. application Ser. No. 16/004,874, filed 11 Jun. 2018, U.S. application Ser. No. 14/969,446, filed 15 Dec. 2015, U.S. application Ser. No. 17/679,688, filed 24 Feb. 2022, and U.S. application Ser. No. 17/896,800, filed 26 Aug. 2022, and U.S. application Ser. No. 18/114,130, filed 24 Feb. 2023, each of which is incorporated in its entirety by this reference, or any other suitable processes performed in any suitable order. The method 200 can be performed with a system as described above and/or any other suitable system.

2. Benefits

The system and method for partially or fully automated buoyant-assisted separation can confer several benefits over current systems and methods.

In a first variation, the technology confers the benefit of enabling any or all of the processes conventionally associated with particle sorting and/or separation applications (e.g., cell separation, cell therapy, cell activation, cell enrichment chemical separation, cell isolation, nucleic acid extraction, sample purification, dead cell or other particle removal, sample preparation, RNA extraction, Leukopak processing, etc.) to be partially or fully automated to users, which can in turn confer the benefits of any or all of: increasing an efficiency with which such processes can take place (e.g., enabling time-sensitive materials to be reliably used), increasing a volume of particles able to be processed, increasing accuracies and/or yields associated with such processes, and/or any other benefits. For instance, the system and/or method can be any or all of the following (e.g., relative to conventional systems and/or methods): faster than conventional (e.g., manual) methods; gentler on cells or other target material; more scalable (e.g., able to process hundreds of milliliters of material at a time, able to process a liter or more of material at a time, etc.); more versatile (e.g., supporting a breadth of starting materials, applications, and/or kits); high yield (e.g., isolating more cells that are ready for activation, expansion, cell culture, molecular assays, and more); easy-to-use (e.g., processing samples semi- or fully automatically, requiring minimal training, reducing manual error, etc.); temporally efficient (e.g., isolating cells from one or more samples simultaneously with less than an hour of processing time per run, with a processing time of less than 90 minutes, with a processing time of between 45 and 90 minutes, with a processing time of less than 45 minutes, with a processing time of between 20 and 50 minutes, with a processing time between any of the aforementioned values and/or other values, etc.); compliant (e.g., meeting requirements for use in researching and/or processing and manufacturing for gene and cell therapy, etc.); and/or conferring of any other benefits.

In a set of examples, an automated instrument and associated method of use enable any or all of the addition and removal of materials, the mixing of materials, the separation of materials, the processing of materials, the collection of materials, and/or any other processes to be fully or partially automated.

In a second variation, additional or alternative to the first, the technology confers the benefit of promoting and/or ensuring a high sterility of any or all of the materials utilized in the system and/or method, such as through the promotion of a closed system implementation.

Figure 15A:
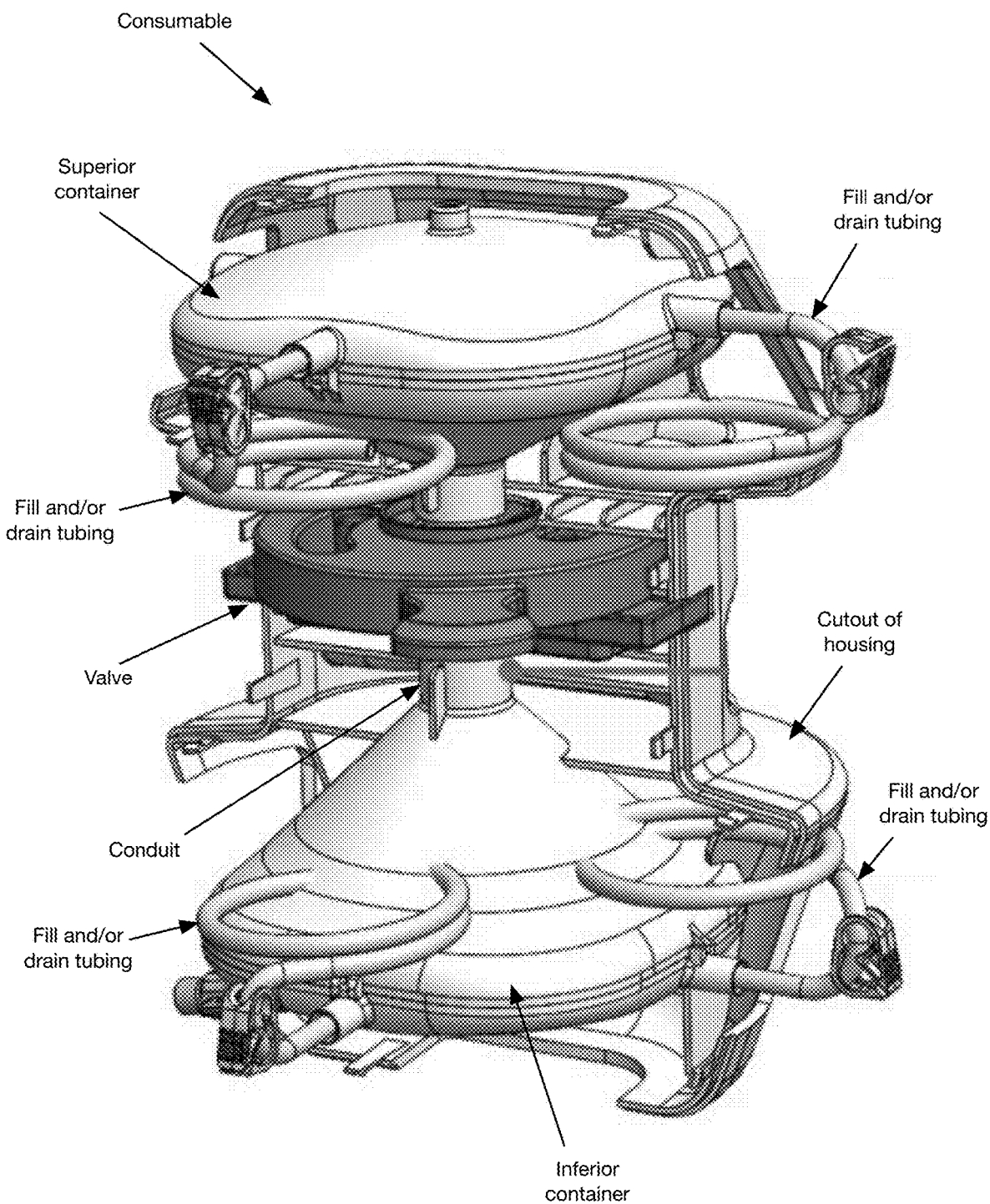
FIGS. 15A-15B depict an example of a consumable with a housing.
Figure 15B:
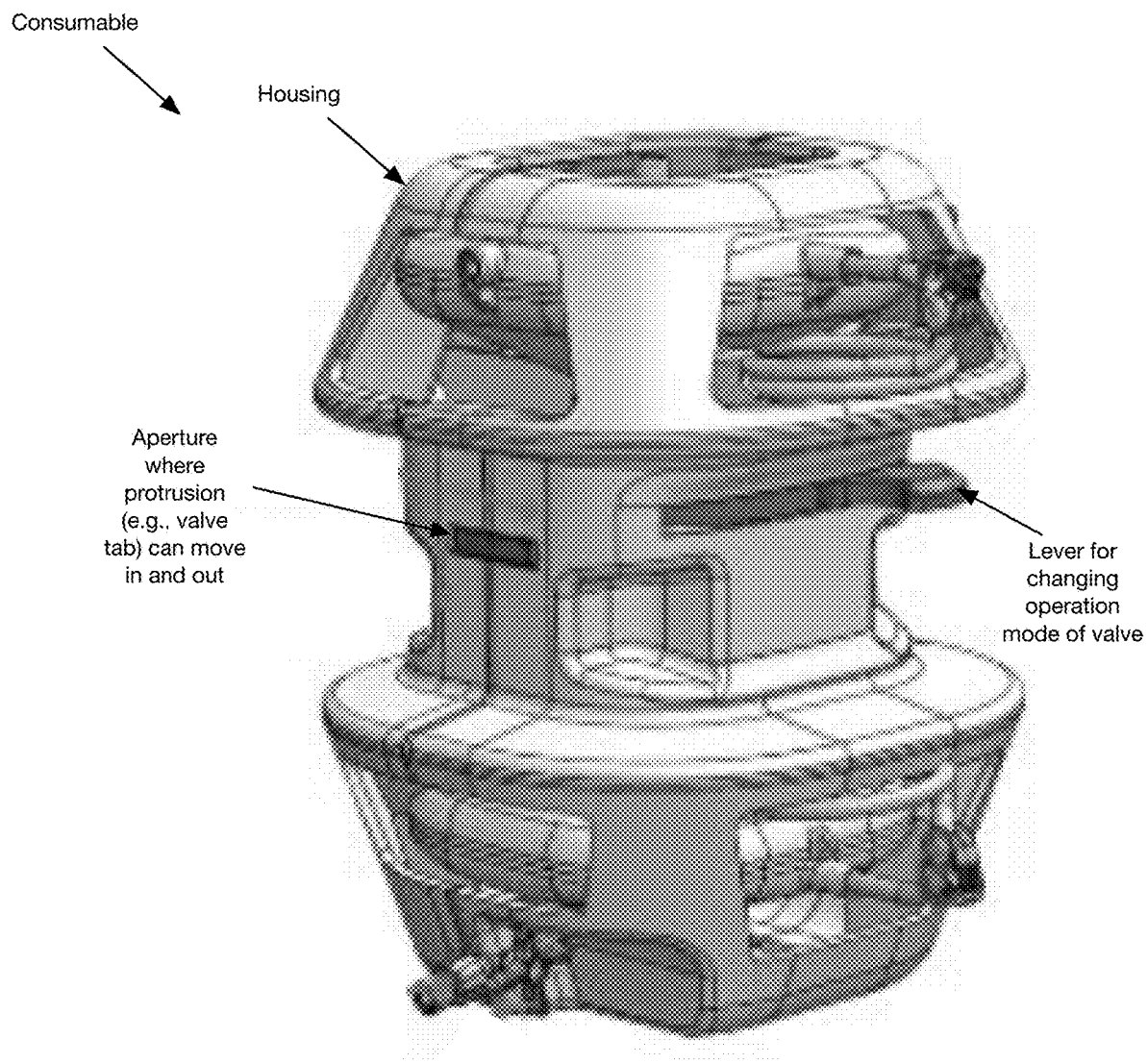

In a set of examples, for instance, the automated instrument is configured with a set of access ports which enable materials to be added to and/or removed from their containers in a closed system, sterile fashion. In a particular example (e.g., as shown in FIGS. 15A-15B, the containers of the consumable interface with tubing (e.g., at both containers) or other conduits, which can enable materials to be added to and/or removed from the containers (e.g., via the access ports, in a closed system fashion, etc.).

Additionally, the automated instrument and/or an accompanying method of use can be configured to interfacing with other closed system components and/or processes such that closed system sterility is preserved among the entire processing of the materials.

In a third variation, additional or alternative to those described above, the technology confers the benefit of enabling and/or optimizing any or all of the processes performed by the automated instrument through the use of buoyant particles. As such, the technology can be configured to optimize (e.g., maximize) collection of buoyant particles and their bound materials, minimize collection of non-buoyant particles and/or non-target materials, and/or confer any other benefits.

In examples, the set of containers and/or associated mixing setup (e.g., in $2^{nd}$ set of container management subsystems) are optimized for use in conjunction with buoyant particles, such as through any or all of: a specific set of geometric properties, a specific set of volume properties, a specific set of mixing protocols and/or mixing features (e.g., angle of mixing, speed of mixing, etc.), and/or any other properties.

In additional or alternative examples, the system and/or method are configured to prevent and/or minimize adhesion of buoyant particles to interior surfaces of the container(s) and/or conduit(s) and/or any other materials that they may contact. In preferred embodiments of the system for instance, any or all of the containers are shaped (e.g., with a particular pitch, with bulb shapes, with a collective hourglass shape, etc.), sized (e.g., in diameter, in height, in width, with a minimum smallest diameter, etc.), constructed (e.g., with minimal friction materials, with smoothed interior surfaces, with coated interior surfaces, etc.), and/or otherwise configured to minimize the amount of buoyant particles that adhere to interior surfaces, thereby maximizing the amount of buoyant particles (e.g., to target materials) that can ultimately be collected.

In specific examples, for instance, each of the containers has dimensions (e.g., length, width, height, largest dimension, etc.) of less than 7 inches, such that the container (optionally with the housing) can fit within the space of a 7" cube. Additionally or alternatively, the container can be sized to fit in a cube having a dimension between 3-12", sized to fit in a non-cuboidal volume, and/or otherwise suitably sized. This can enable, for instance, the automated instrument to be configured for use as a desktop device. Additionally or alternatively, the collective set of containers can be dimensioned as described above, the entire consumable (e.g., containers with housing and conduit) can be dimensioned as described above, and/or the components can have any other suitable dimensions.

The containers can be separate, connected (e.g., via a conduit), part of a single part/piece (e.g., an hourglass-shaped single container defining multiple chambers), and/or otherwise arranged.

Figure 6:
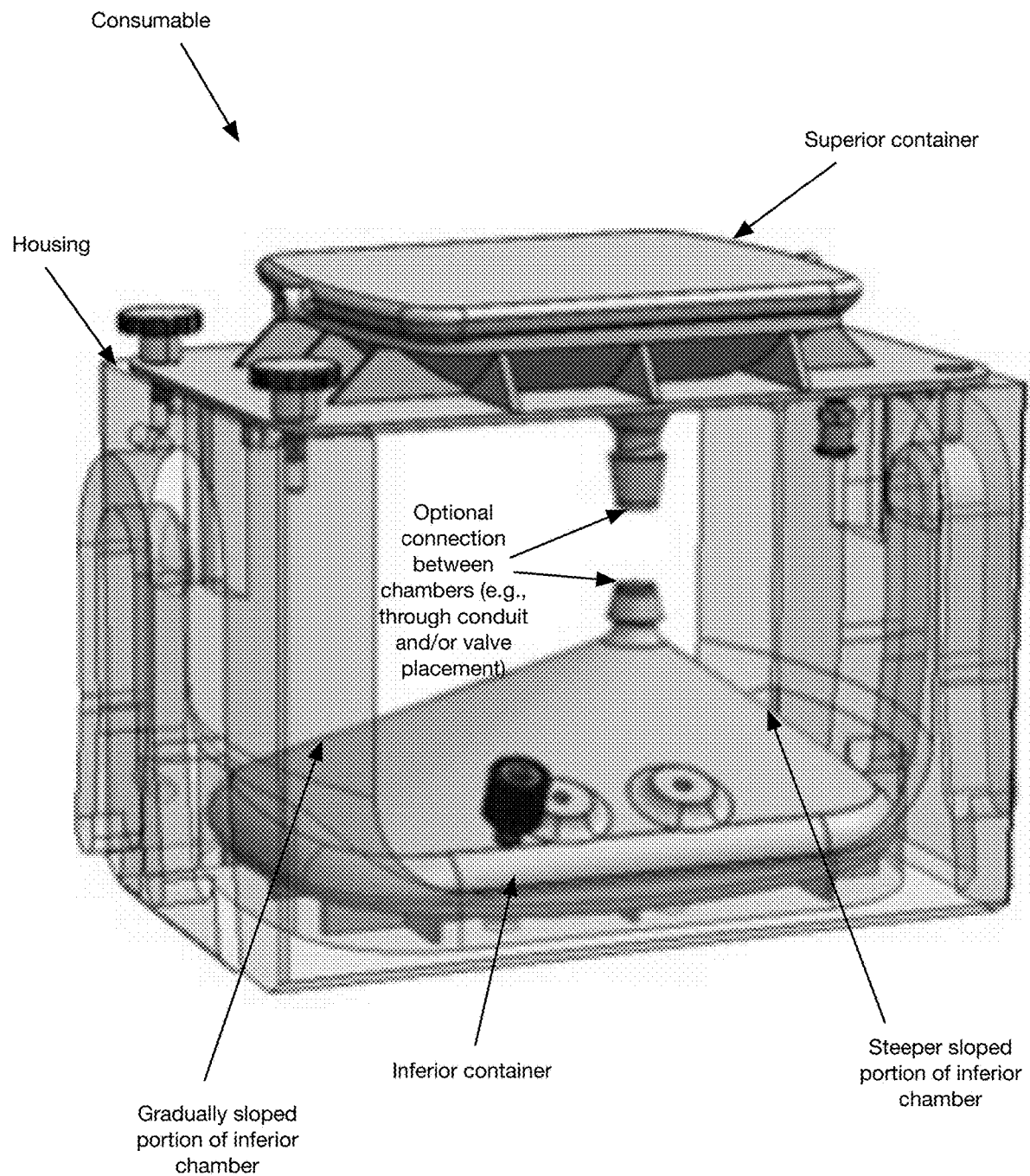
FIG. 6 depicts a first example of the geometrical properties of an inferior chamber and a superior chamber of a container.
Figure 7:
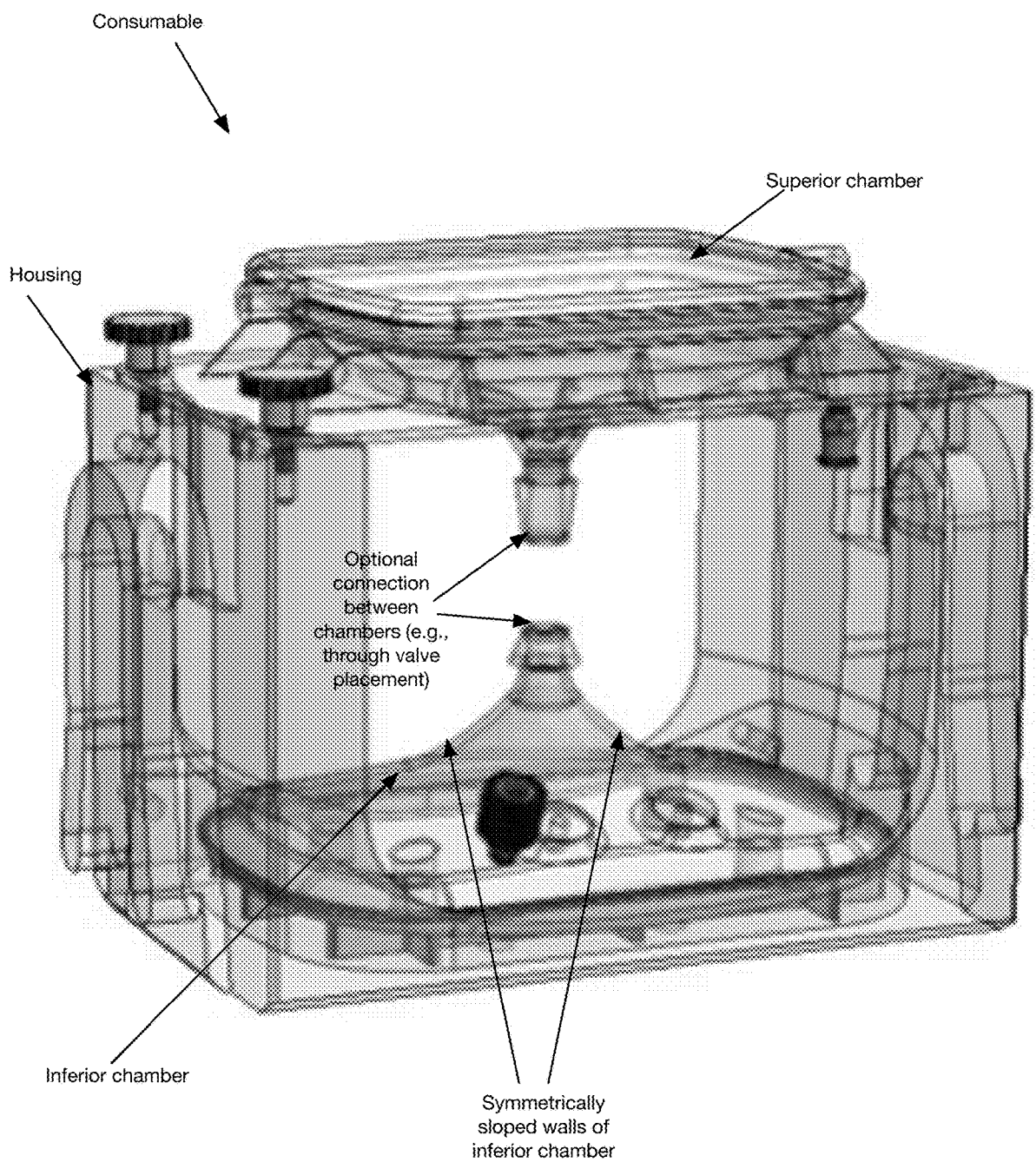
FIG. 7 depicts a second example of the geometrical properties of an inferior chamber and a superior chamber of a container.
Figure 8:
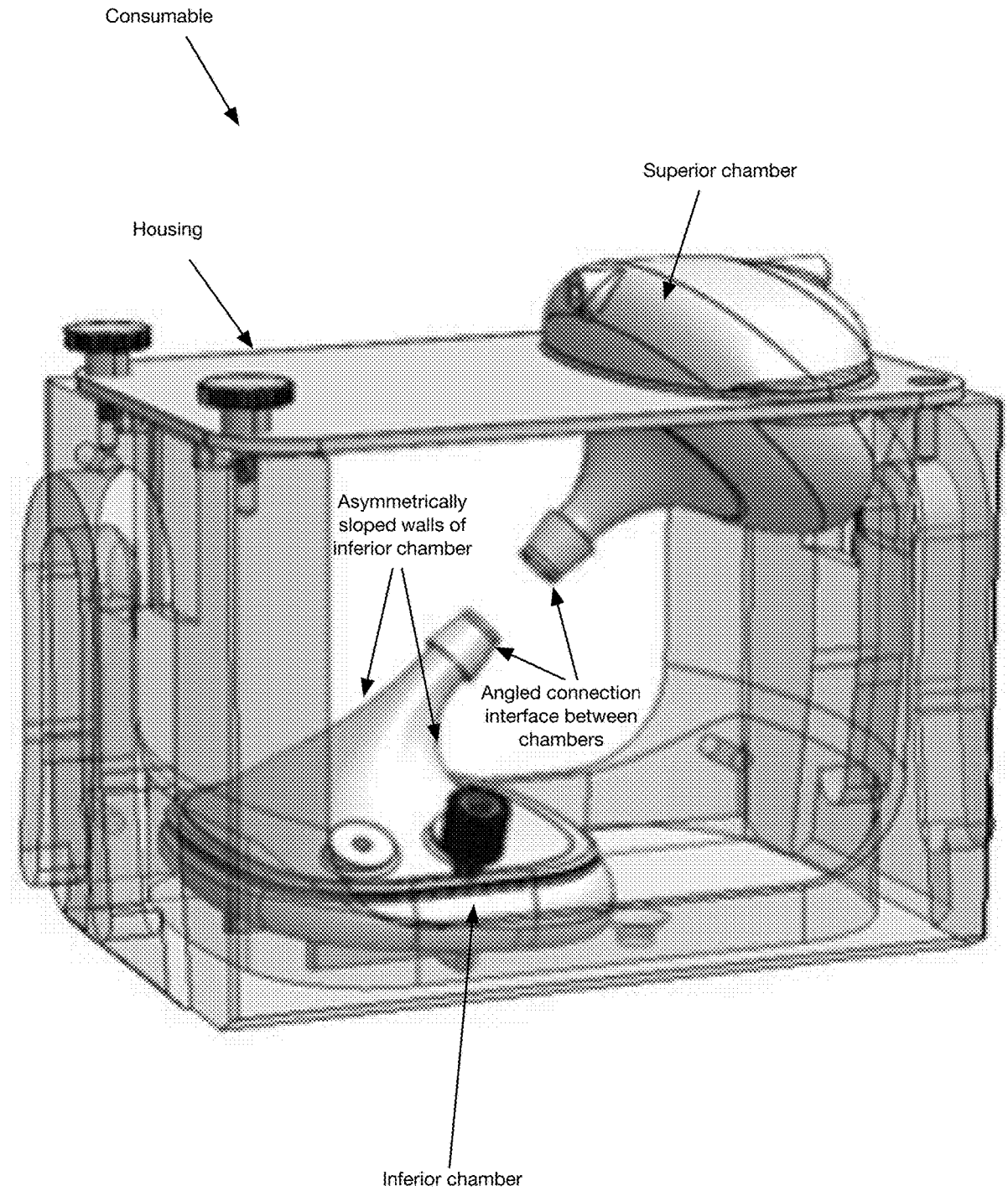
FIG. 8 depicts a third example of the geometrical properties of an inferior chamber and a superior chamber of a container.
Figure 9A:
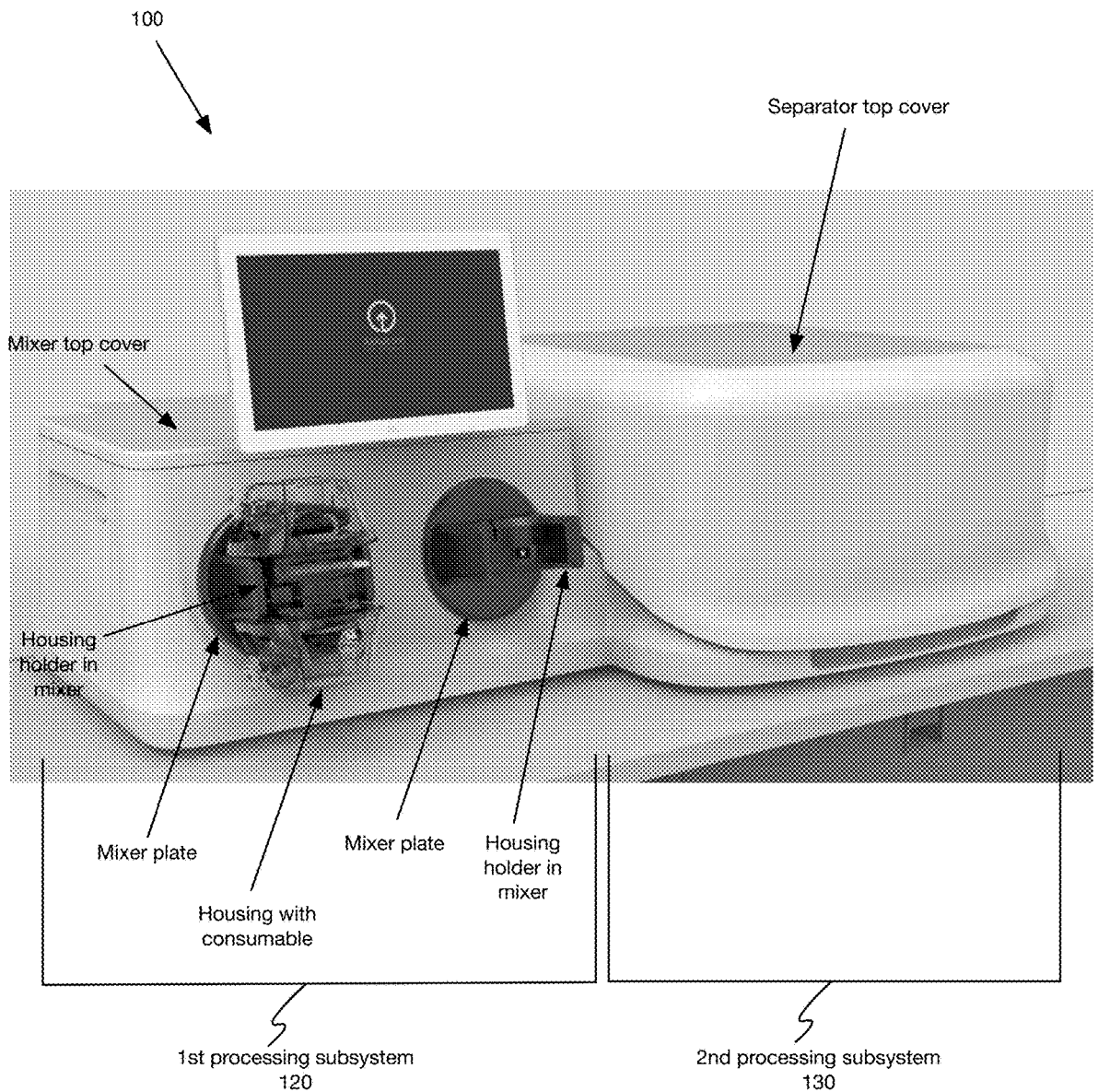
FIGS. 9A-9B depict an example of the automated instrument including $1^{st}$ and $2^{nd}$ processing subsystems.
Figure 9B:
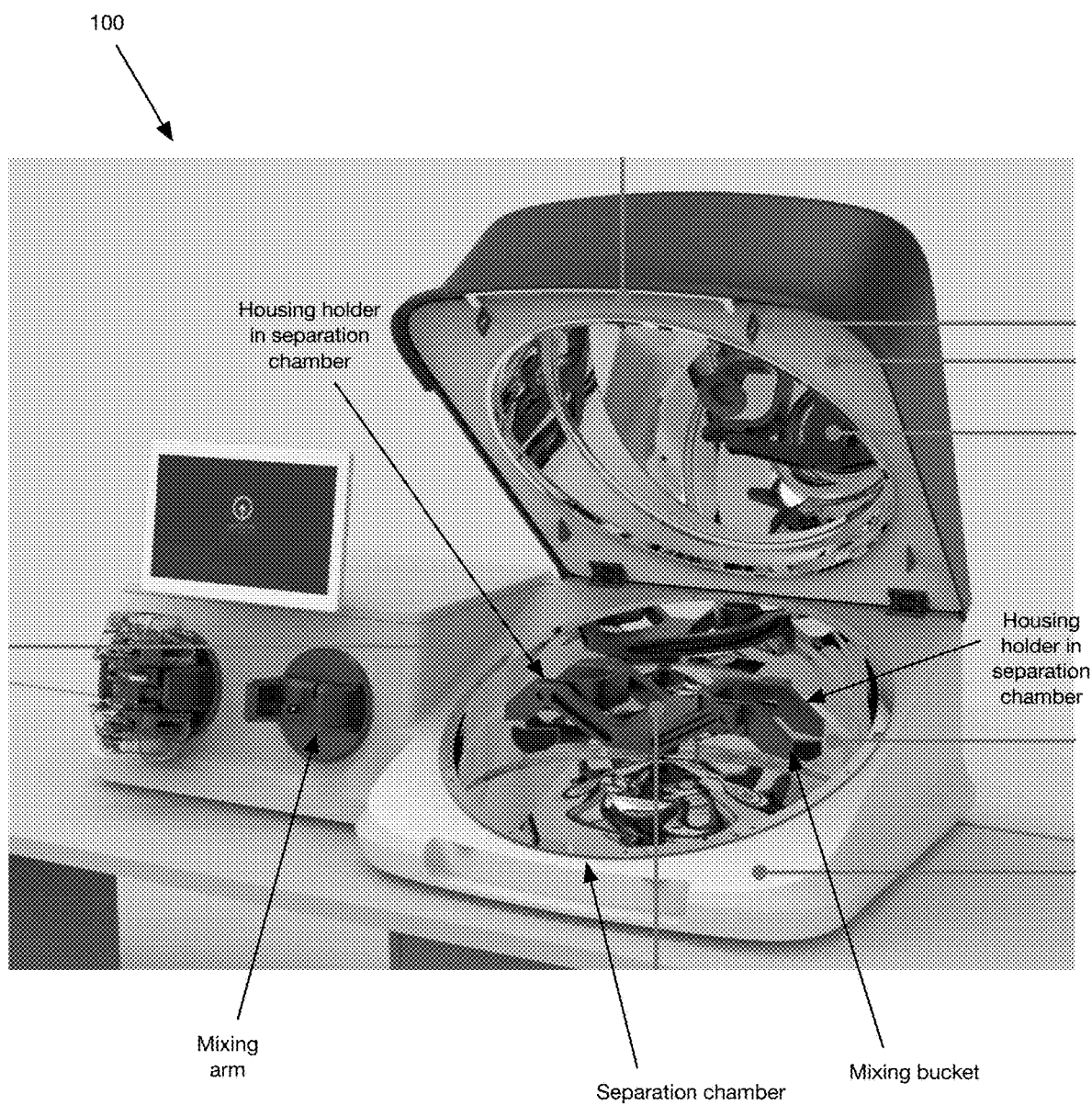
Figure 13A:
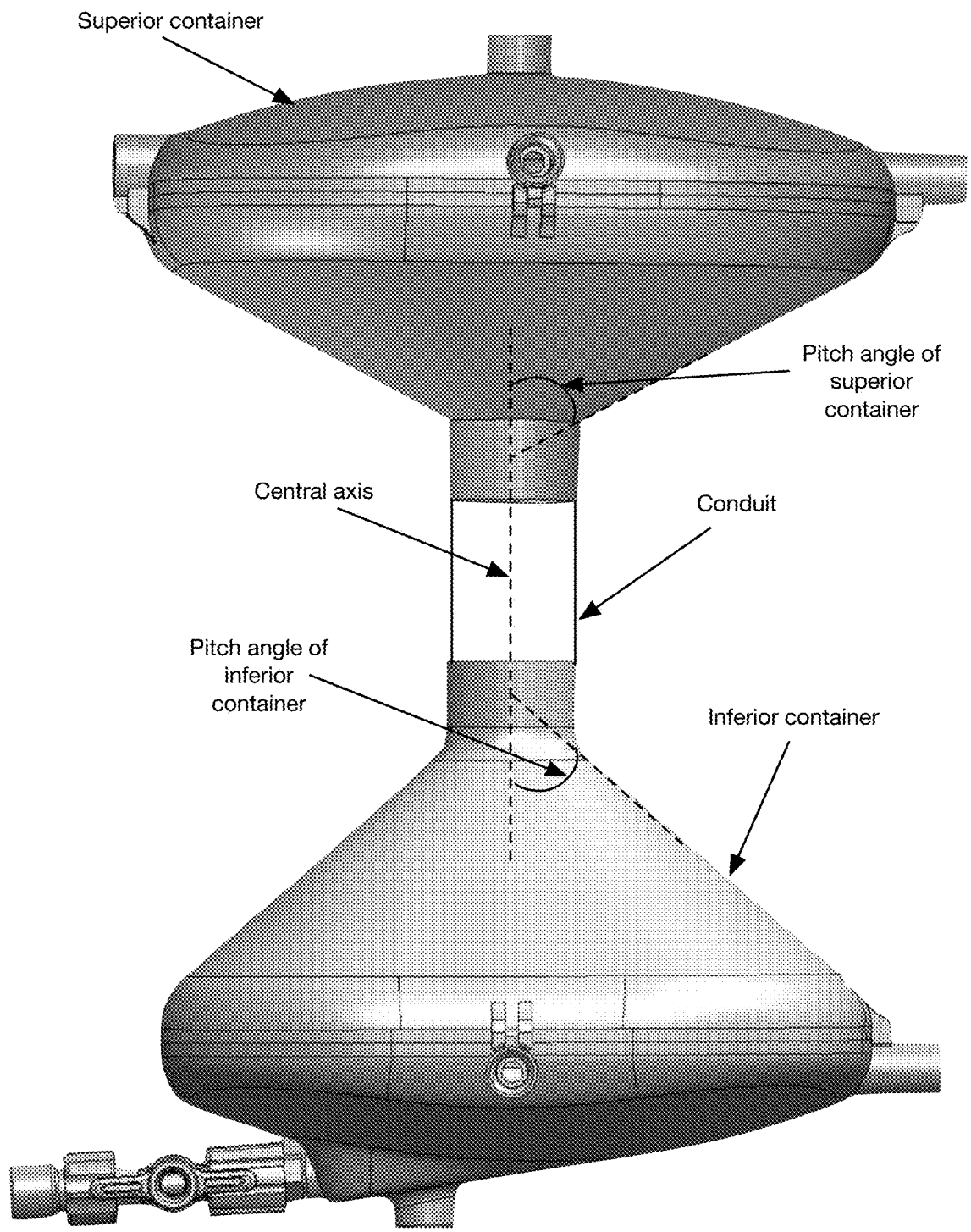
FIGS. 13A-13B depict an example of a $1^{st}$ container, $2^{nd}$ container, and flexible conduit of a consumable.
Figure 13B:
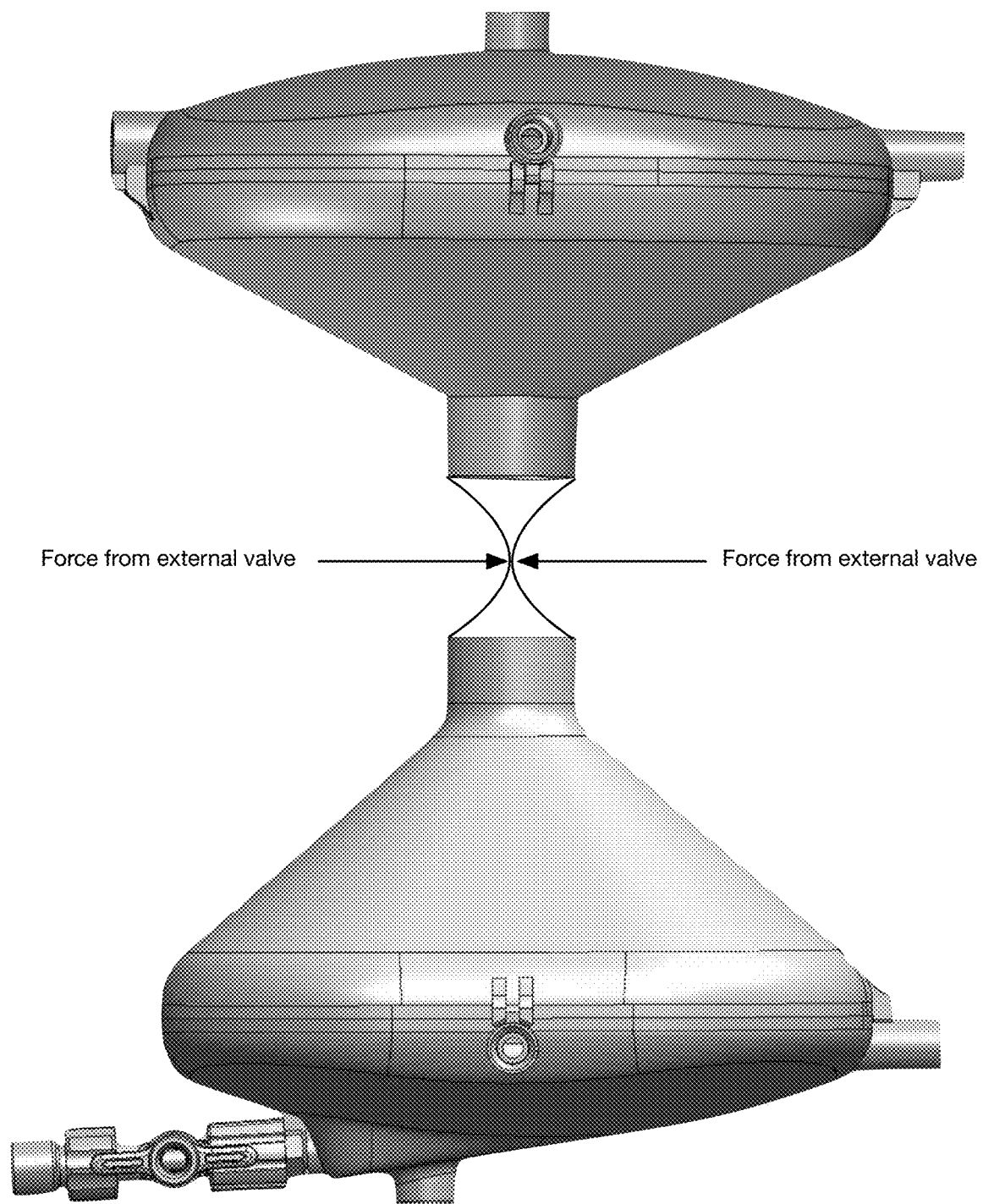

In a specific set of examples (e.g., as shown in FIGS. 6-8, as shown in FIGS. 13A-13B, as shown in FIGS. 15A-15B, etc.), one or both containers are shaped to have a sloped profile (equivalently referred to herein as a pitch) with decreasing diameter in a direction approaching the other respective container (e.g., decreasing diameter as the superior container approaches the inferior container, decreasing diameter as the inferior container approaches the superior container, with a smallest diameter closest to a flexible conduit connecting the containers, etc.). This can function to guide buoyant particles from one container to the other (e.g., from the inferior container to the superior container), minimize an interior surface area at which buoyant particles can adhere (e.g., during transit, during mixing, etc.), create flow and/or increase contact of the bulk volume along interior surfaces during mixing (e.g., to wipe/remove buoyant particles from the interior surface and guide into the flexible conduit), and/or otherwise improve collection of the buoyant particles. The containers have the same shape relative to each other; different shapes relative to each other (e.g., as shown in a higher pitch of the inferior container relative to the superior container in FIGS. 13A-13B); a symmetric shape (e.g., about an axis running through a center of the flexible conduit, such as shown in FIG. 7, such as shown in FIGS. 13A-13B, such as shown in FIGS. 15A-15B, etc.); an asymmetric shape (e.g., about an axis running through a center of the flexible conduit, such as shown in FIGS. 6 and/or 8, etc.); and/or be otherwise shaped. Additionally or alternatively, the containers can have the same, similar, and/or different sizes relative to each other; the same, similar, and/or different materials relative to each other; and/or can be otherwise suitably configured.

In a fourth variation, additional or alternative to those described above, the technology confers the benefit of optimizing outcomes associated with use of the automated instrument, which can function, for instance, to prevent the consumable from being processed while it is in a non-optimal and/or incorrect state. This is preferably enabled through ensuring that the valve is in a particular state to enable coupling of the consumable with the automated instrument, but can additionally or alternatively be enabled by: preventing running of a protocol unless the valve is in a certain configuration, and/or otherwise operating the automated instrument to improve outcomes.

Figure 14A:
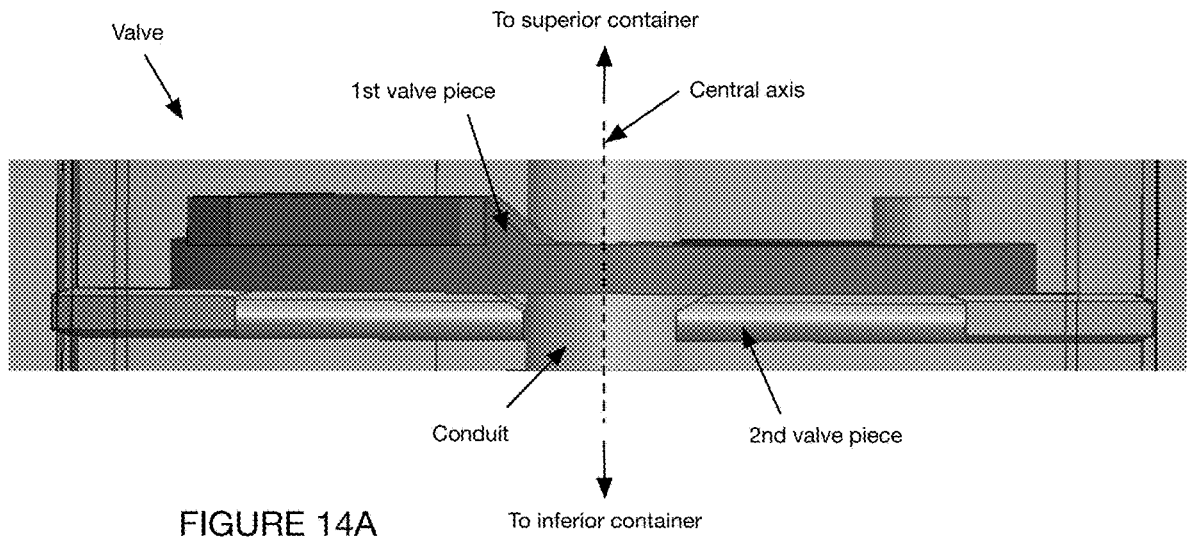
FIGS. 14A-14B depict an example of a valve for use in a consumable.
Figure 14B:
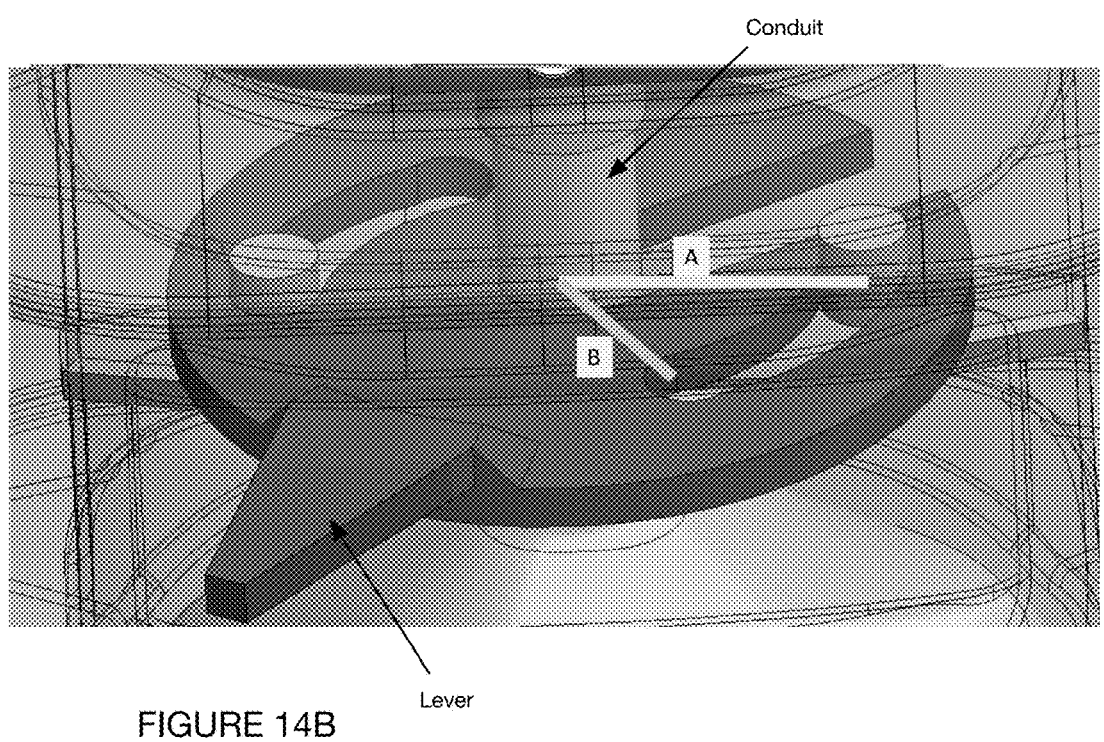

In examples, for instance, the consumable can only physically connect to a pre-separation component (e.g., $1^{st}$ mixing subsystem) of the automated instrument when the valve is in a closed configuration, and the consumable can only physically connect to a separation component (e.g., $2^{nd}$ mixing subsystem) of the automated instrument when the valve is in an open configuration. This is preferably enabled (e.g., as shown in FIGS. 14A-14B) through the positioning of a set of notches that move in and out depending on the configuration of the valve, but can alternatively be otherwise suitably enabled.

In alternative examples, the valve is configured to open on its own, such as upon reaching a certain set of conditions (e.g., multiple of g-force, temporal conditions, etc.) associated with a separation protocol (e.g., negative selection, positive selection, human T cell negative selection, human T cell positive selection, etc.), thereby enabling the valve to open naturally at the proper time. In a specific example, for instance, the valve includes a spring-actuated mechanism that opens the conduit between the containers once a certain g-force is experienced in the separation process.

Additionally or alternatively, the system and method can confer any other benefit(s).

3. System

As shown in FIG. 1, a system 100 for partially or fully automated, buoyancy-assisted separation includes and/or interfaces with an automated instrument 110. Additionally or alternatively, the system can include and/or interface with any or all of: a set of buoyant particles 160, a set of containers 150 (individually and/or collectively equivalently referred to herein as a consumable), a $1^{st}$ container management subsystem 120 (equivalently referred to herein as a $1^{st}$ processing subsystem and/or a $1^{st}$ mixing subsystem), a $2^{nd}$ container management subsystem 130 (equivalently referred to herein as a $2^{nd}$ processing subsystem and/or a $2^{nd}$ mixing subsystem), a user interface subsystem 140, and/or any other components.

The system functions to facilitate, and further preferably optimize, one or more actions associated with the processing of a sample through the use of automation and buoyant particles. In preferred variations, for instance, the system functions to perform the buoyant separation of particles within a sample through automation as implemented with an automated instrument. Additionally, the system can function to: increase an efficiency associated with any or all processes, increase a volume and/or yield associated with any or all processes (e.g., as compared with manual performance of the processes), and/or can perform any other suitable functions.

3.1 System: Automated Instrument 110

The system 100 includes and/or interfaces with an automated instrument 110, which functions to enable any or all of: the customization of workflows and/or protocols, an increase in batch size (e.g., multiple containers, multiple Leukopaks, etc.) able to be processed in single protocols, an assurance of sterility of the same through closed system workflows, faster workflows and/or greater yields relative to conventional and/or manual systems, simpler preparation and/or collection of materials after separation (e.g., through non-magnetic process implementations), and/or any other outcomes.

The automated instrument 110 can optionally be configured to interface with (e.g., in a modular fashion) other instruments, storage containers, and/or sites that materials of the sample may be present and/or processed at. This can function, for instance, to maintain sterility of the sample (e.g., through a fully closed system implementation among instruments).

The automated instrument 110 is preferably configured for automation (e.g., partial automation, full automation, etc.) of at least particle separation processes (e.g., cell separation, isolation of a set of target materials from a remainder of a sample, etc.), and further preferably for enabling high performance positive selection (e.g., cell activation) applications, high performance negative selection applications, any other applications, and/or any combination of applications.

The automated instrument 110 is further preferably configured for sterile, closed system treatment of the materials handled by the automated instrument, which can be enabled through any or all of: one or more components of the automated instrument (e.g., Luer locks that enable the sterile addition and removal of materials from containers), manufacturing processes used to produce the automated instrument (e.g., sterile welding), and/or any other features of the automated instrument.

In preferred variants, the automated instrument includes a set of container management subsystems (e.g., as described below), such as, but not limited to a $1^{st}$ container management subsystem 120 and/or a $2^{nd}$ container management subsystem 130. The container management subsystems preferably function to manipulate (e.g., move, translate, rotate, actuate, heat, cool, etc.) one or more containers (e.g., individually, collectively, etc.) of the system 100, which can function (e.g., through combined motions according to a protocol) to: mix contents of one or more containers; facilitate movement of buoyant particles thereby causing separation of buoyant-particle-bound materials from a remainder of a bulk volume; add and/or remove contents from one or more containers; heat, cool, and/or otherwise process materials in the container(s); and/or otherwise process materials in the container(s).

The automated instrument can include any number of components configured to enable any or all of the functions as described above and/or below, such as, but not limited to: one or more actuators (e.g., motors, robotic arms, electrically-activated components, pneumatically-activated components, hydraulically-activated components, etc.), power sources, fixtures (e.g., holders for containers), and/or any other components.

Additionally or alternatively, the automated instrument can include and/or interface with any other components.

3.2 System: Set of Containers 150

Figure 3A:
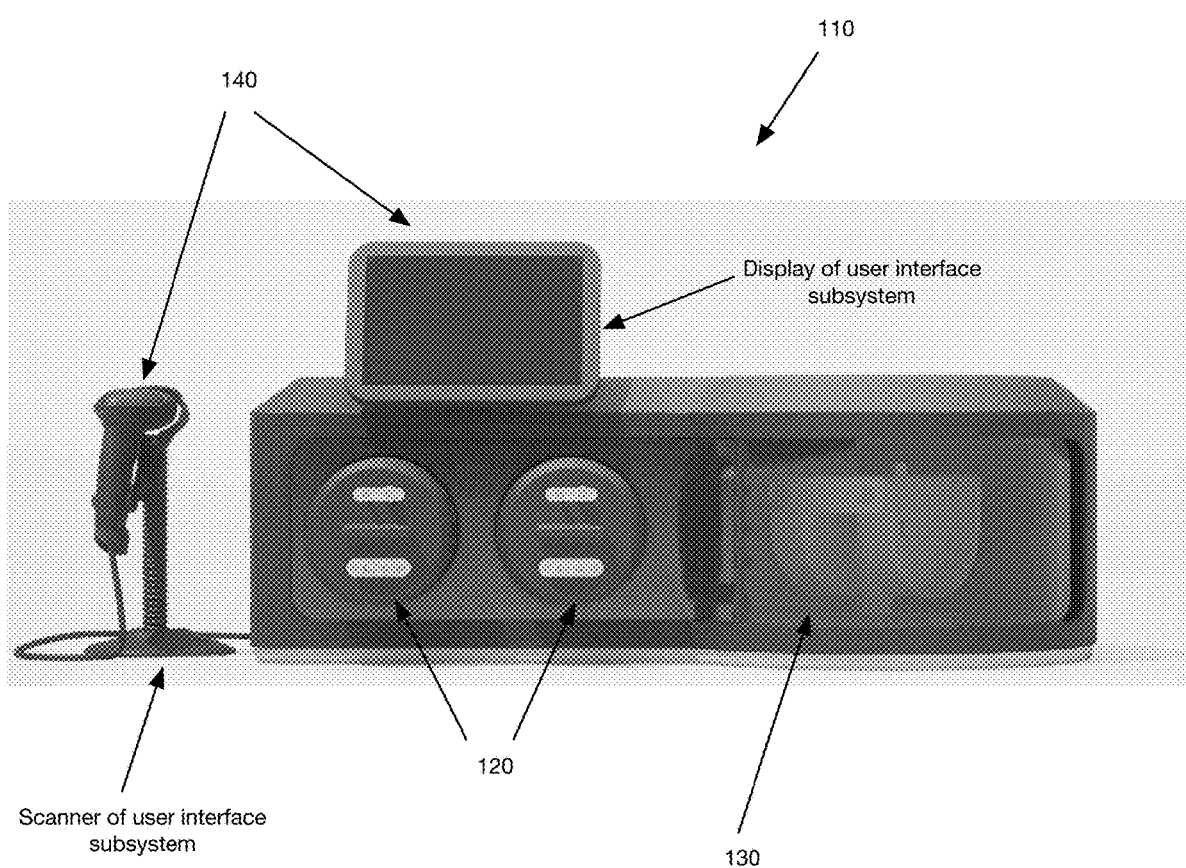
FIGS. 3A-3M depict a variant of a system for partially or fully automated buoyancy-assisted separation.
Figure 3B:
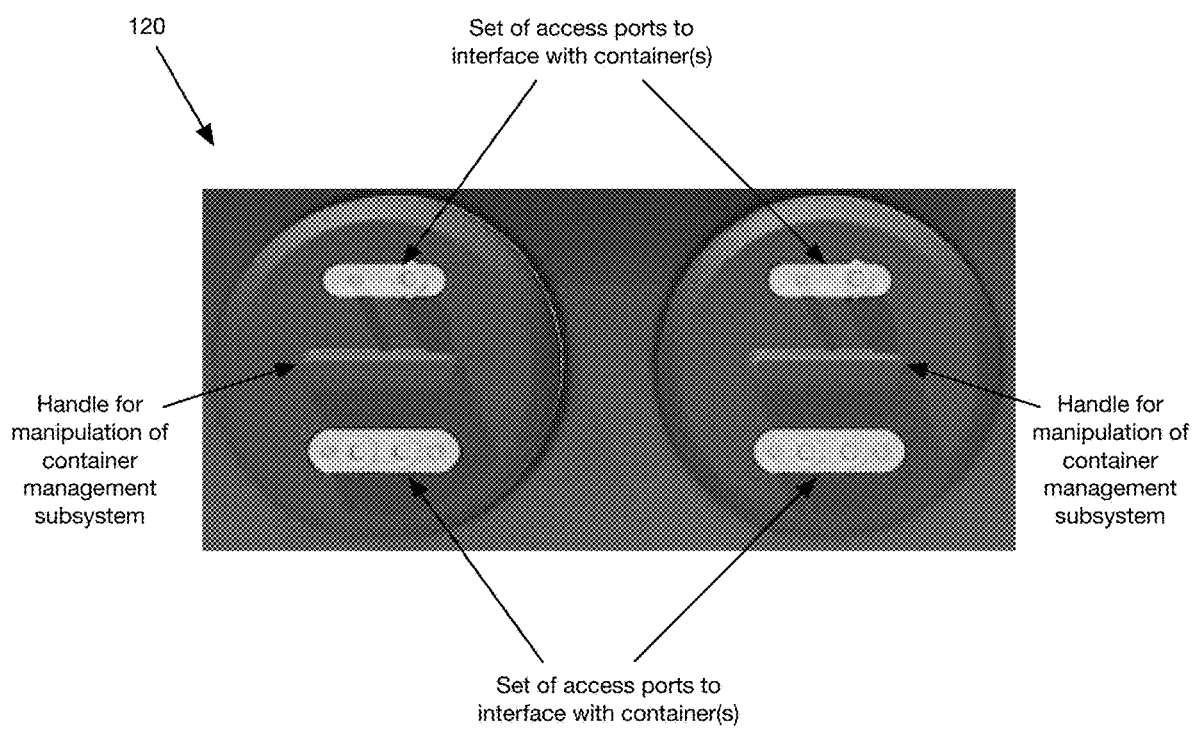
Figure 3C:
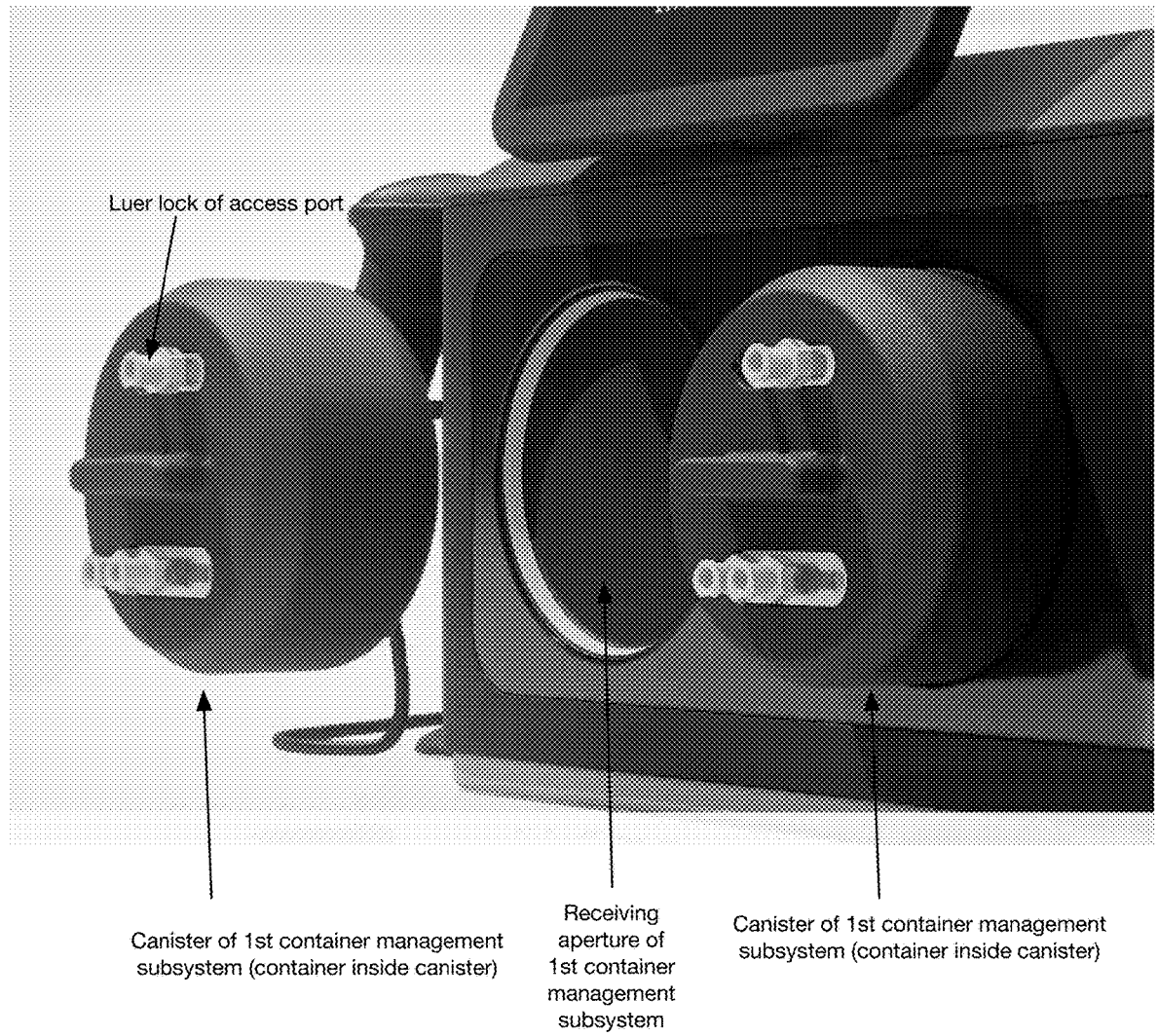
Figure 3D:
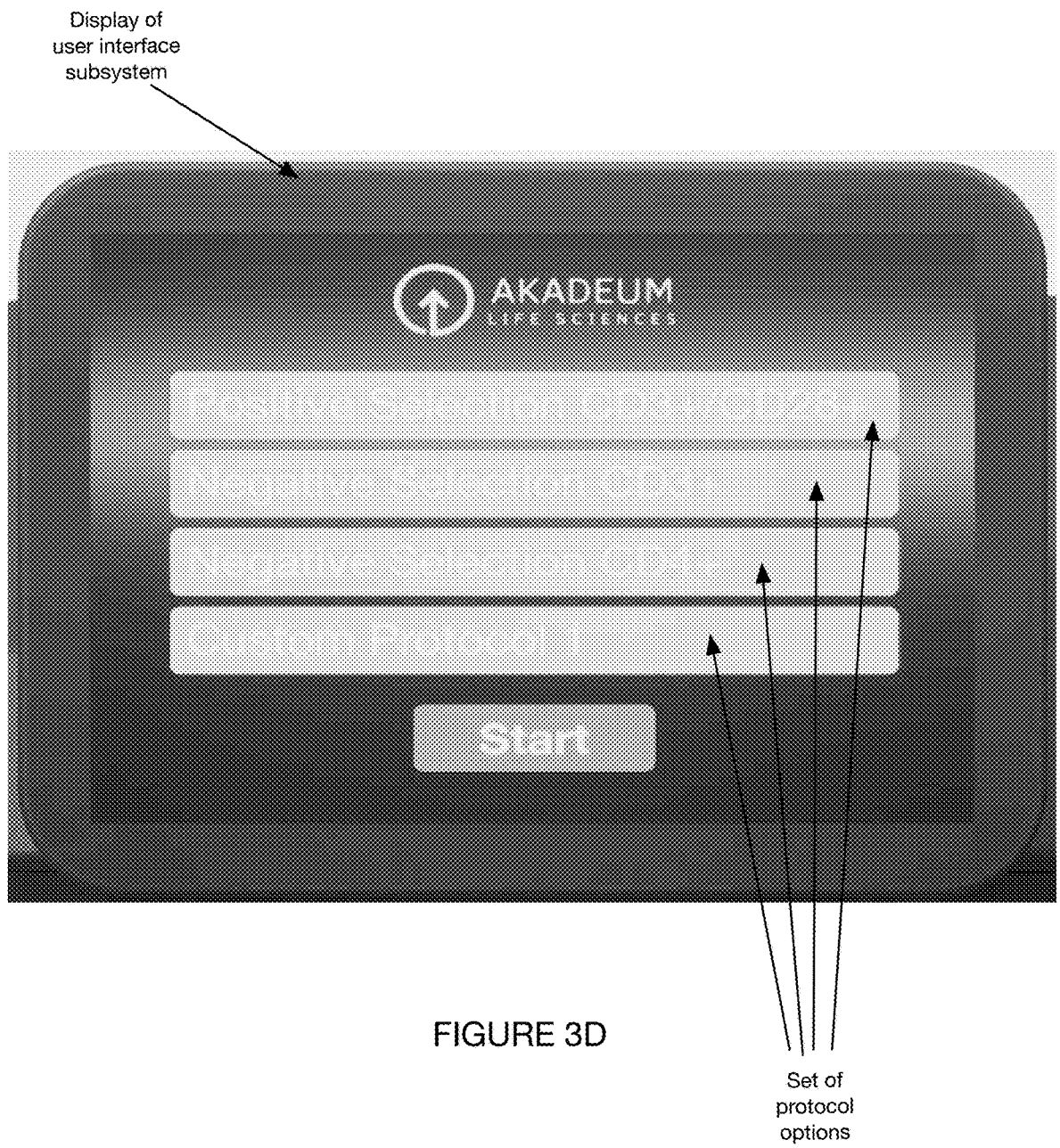
Figure 3E:
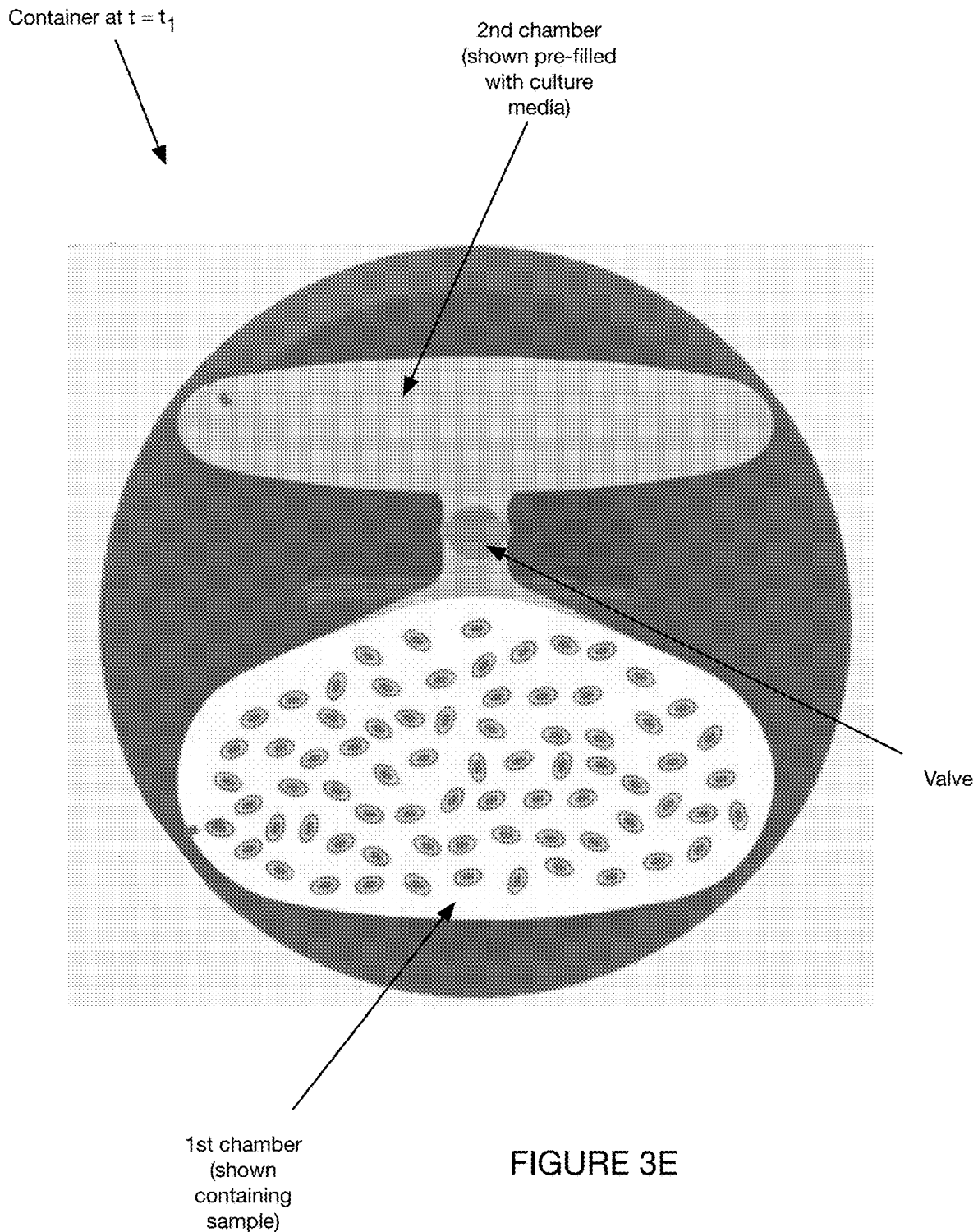
Figure 3F:
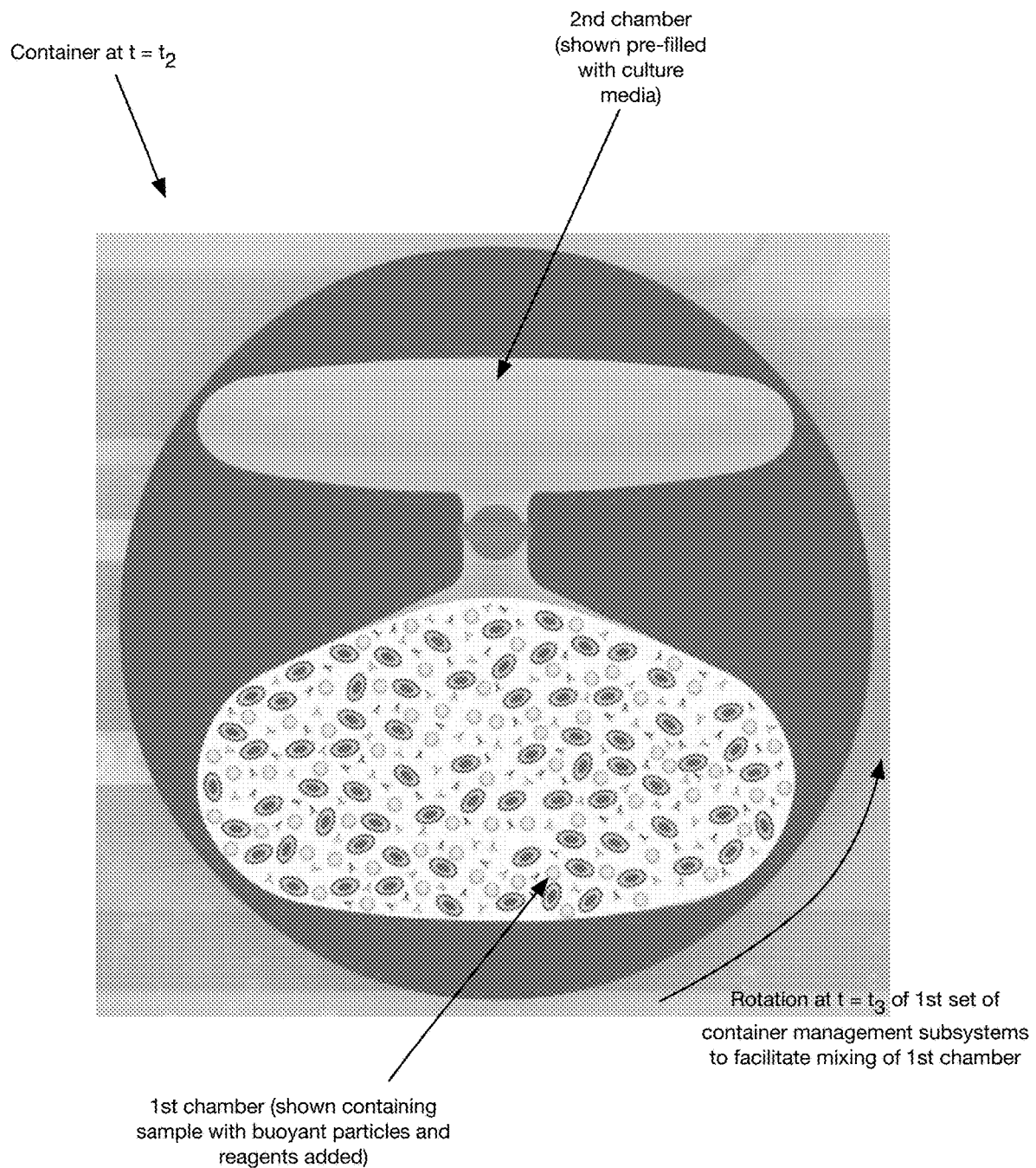
Figure 3G:
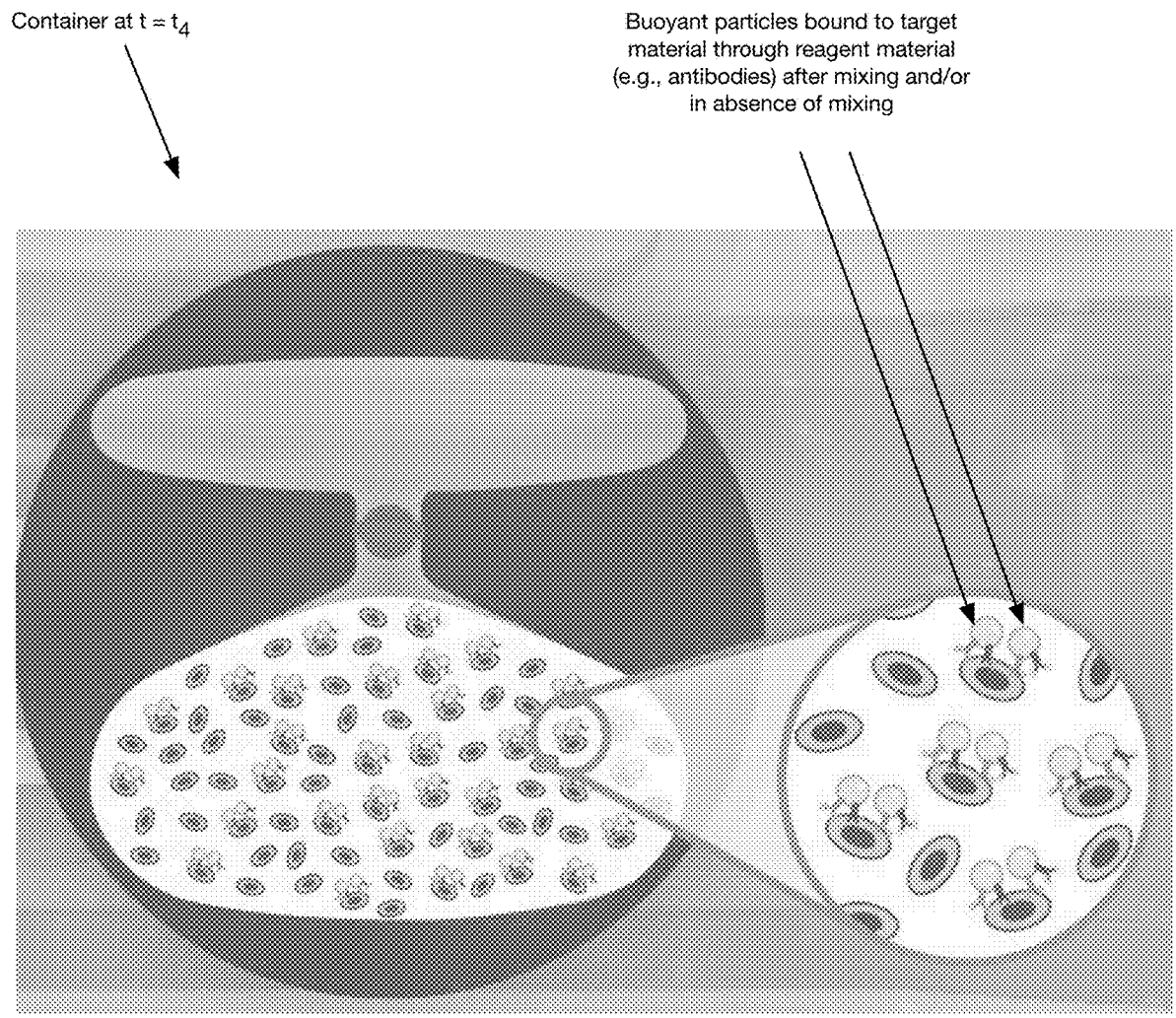
Figure 4:
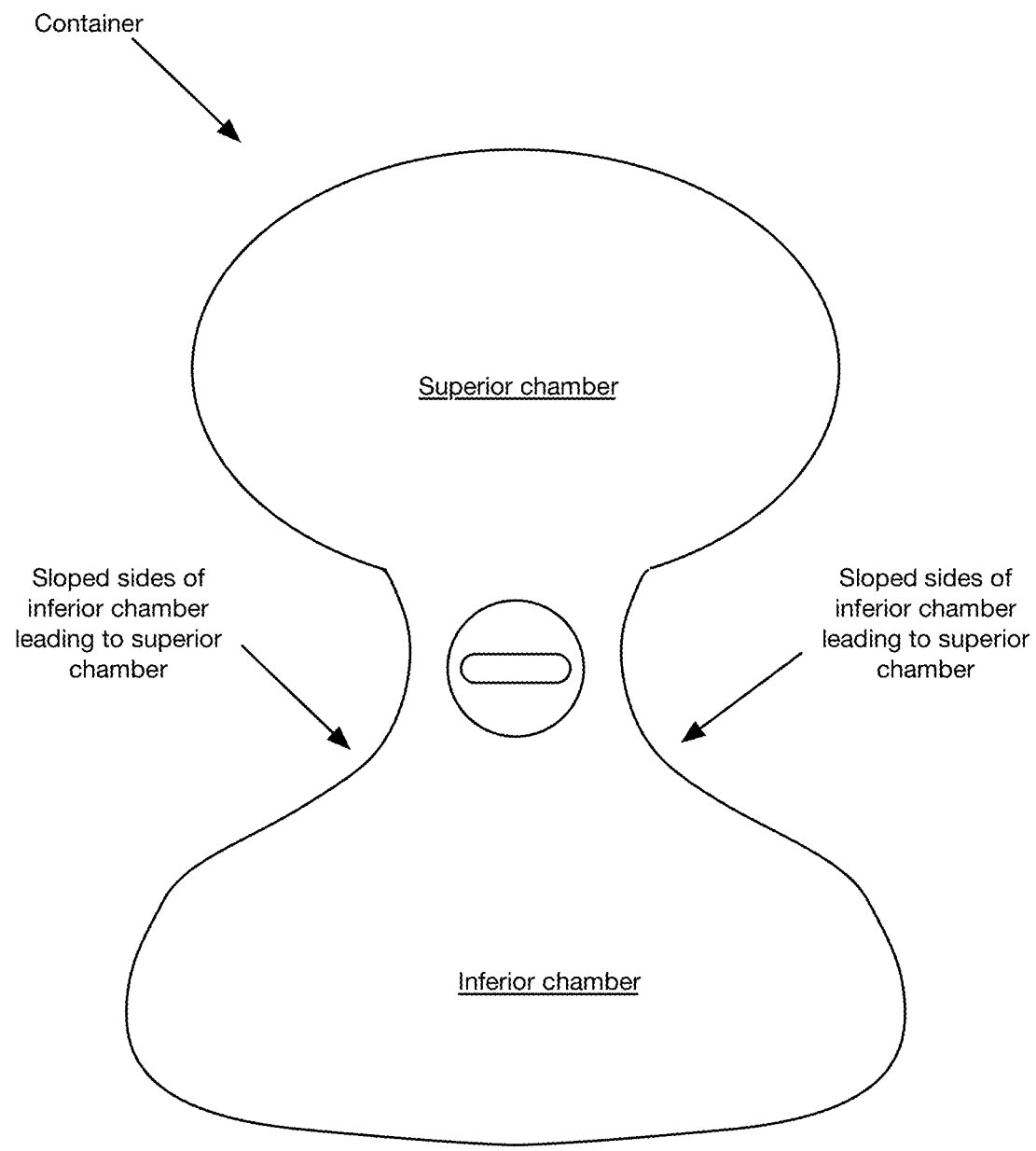
FIG. 4 depicts a variant of a container for use in partially or fully automated buoyancy-assisted separation.
Figure 5:
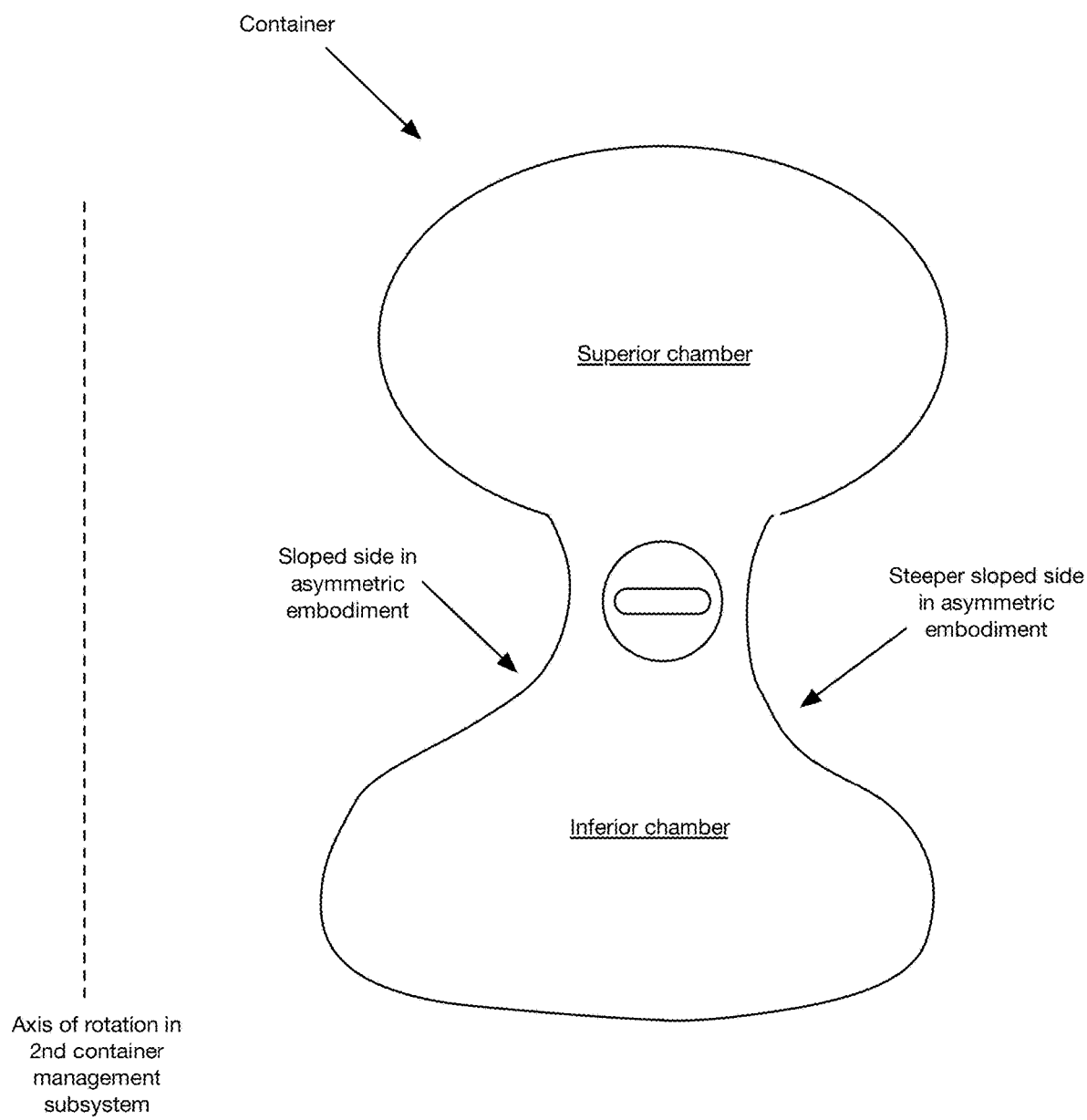
FIG. 5 depicts a variant of a container for use in partially or fully automated buoyancy-assisted separation.

The system preferably includes and/or interfaces with a set of containers 150 (e.g., as shown in FIG. 1, as shown in FIGS. 3E-3G and 3K-3M, as shown in FIG. 4, as shown in FIG. 5, as shown in FIGS. 13A-13B, as shown in FIGS. 15A-15B, etc.) where the set of containers functions to contain the materials processed by the automated instrument (e.g., during the method 200). The set of containers can further function to enable and/or facilitate any or all of: sterile (e.g., closed system) treatment of the materials; separation of materials within a sample (e.g., through separable chambers, through sealing of chambers, through a valve separating chambers, etc.); an optimized collection and/or distribution of target particles within a portion of the container (e.g., through geometric properties of the containers, through materials selections of the container, etc.); and/or any other outcomes.

The set of containers can collectively (e.g., with the housing, with a connecting conduit, with other components such as a valve, etc.) be referred to herein as a consumable. The consumable can be single-use, reusable, and/or have any suitable number of uses.

In a preferred set of variants, the consumable includes a superior container, an inferior container, a conduit connecting the superior and inferior containers, a housing, a valve, and/or any other components.

Each of the containers preferably defines one or more chambers (equivalently referred to herein as cavities), which function to contain the contents of the containers, but can additionally or alternatively be otherwise configured. In a preferred set of variants, each container defines a single chamber. In alternative variants, one or more containers defines multiple chambers and/or is configured to be separable (e.g., through the opening and closing of a valve, through heat sealing, through mechanical separation, etc.) into multiple chambers.

Each of the containers is preferably a rigid (e.g., non-deformable, non-elastic, non-flexible, etc.) container (e.g., rigid-walled container), such as a container constructed from materials having any or all of: a stiffness (e.g., shear modulus, Young's modulus, etc.) above a predetermined threshold (e.g., Young's modulus greater than 1 Giga-Pascals [GPa], Young's modulus greater than 0.5 GPa, Young's modulus greater than 1.5 GPa, Young's modulus between 1-10 GPa, Young's modulus between 1-5 GPa, etc.); an elasticity below a predetermined threshold; a wall thickness greater than a predetermined threshold (e.g., greater than 0.25 mm, greater than 0.5 mm, greater than 0.75 mm, greater than 1 mm, greater than 2 mm, between 2-3 mm, within ranges defined by any of the aforementioned values, etc.); and/or any other features. In a preferred set of variants, each of the containers is constructed from a plastic or other polymeric material (e.g., Polycarbonate [PC], Polyvinyl Chloride [PVC], etc.).

In alternative variants, one or more of the set of containers can be constructed from at least partially deformable (e.g., flexible, expandable, pliable, thin-walled, etc.) materials, which can be configured to confer a variable volume capacity (e.g., expandable, shrinkable, etc.) to the container(s). This can include materials, for instance, having a Young's modulus below a predetermined threshold (e.g., Young's modulus less than 1 GPa, Young's modulus less than 0.75 GPa, Young's modulus less than 0.5 GPa, etc.); containers having a wall thickness less than a predetermined threshold (e.g., less than 1 millimeters [mm], less than 0.5 mm, less than 0.25 mm, etc.); materials having an elasticity and/or flexibility above a predetermined threshold; and/or any other materials. Additionally or alternatively, the any or all of the set of containers can be constructed from rigid materials (e.g., plastic, polymer, metal, etc.), semi-rigid materials, a combination of materials (e.g., flexible chamber coupled with a rigid chamber), and/or any other materials.

In one set of variants, for instance, the set of containers includes a set of flexible bags, where the bags can be expandable, deformable, separable into multiple chambers, and/or otherwise manipulated.

Additionally or alternatively, the containers can have any other suitable form factors and/or be constructed from any suitable materials.

The consumable preferably includes and/or is configurable in a set of multiple portions (e.g., multiple chambers, multiple containers, etc.), which can be any or all of: fluidly connected (e.g., during a portion of the method, in response to opening of a valve arranged between the portions, etc.), fluidly isolated (e.g., during a portion of the method, while a valve separating the portions is in a closed configuration, etc.), completely separable (e.g., into 2 separate bags after a sealing and/or separation process), able to alternate between configurations (e.g., from fluidly isolated to fluidly coupled throughout the opening of a valve), and/or otherwise configured. Alternatively, any or all of the set of containers can include a single portion (e.g., single chamber).

The multiple portions can be any or all of: associated with the same or different heights, the same or different volumes, the same or different geometries, the same or different materials, and/or can have any other properties.

The consumable preferably includes a set of one or more conduits (e.g., tubes, cylinders, etc.) configured to fluidly connect two or more containers of the set of containers. The set of conduits can be flexible (e.g., less rigid than the containers), rigid, or any combination. In a preferred set of variants (e.g., as shown in FIGS. 13A-13B), the consumable includes a conduit (e.g., flexible conduit, PVC conduit, etc.) arranged between the inferior container and the superior container, such that a fluidic connection between the containers can be selectively enabled and disabled through a valve (e.g., as described below). In specific examples, the conduit includes a flexible conduit constructed from PVC that enables both deformability of the flexible conduit by action of a valve (e.g., as described below) and prevention of sticking of interior walls and/or kinking in the flexible conduit.

In a preferred set of variations (e.g., as shown in FIGS. 3E-3G and 3K-3M, as shown in FIG. 4, as shown in FIG. 5, etc.), the container includes at least a $1^{st}$ container defining at least a $1^{st}$ chamber, and a $2^{nd}$ container defining at least a $2^{nd}$ chamber, where the $2^{nd}$ container (equivalently referred to herein as the superior container) is arranged superior to the $1^{st}$ container (equivalently referred to herein as the inferior container). This can enable the buoyant particles, through flotation, to enter the $2^{nd}$ chamber from the $1^{st}$ chamber (e.g., in response to a valve connection between chambers being opened). This arrangement can further be configured to prevent non-buoyant particles and/or materials not bound to buoyant particles to travel into the superior chamber naturally (e.g., under gravity, without inversion of the container, etc.). In a set of examples, the $2^{nd}$ chamber (equivalently referred to herein as the superior chamber) contains fluid (e.g., media) (a.k.a. is pre-filled) prior to fluidly connecting the superior chamber with the $1^{st}$ chamber (equivalently referred to herein as the inferior chamber), where this fluid (e.g., pre-filled culture media) functions to enable and encourage sample materials to enter the superior chamber once the valve is opened. Additionally or alternatively, the superior chamber can be absent of fluid, deflated, inflated with gas, and/or otherwise configured.

Pre-filling the $2^{nd}$ chamber can further function to expand (e.g., unfurl, open, etc.) a flexible conduit arranged between the $1^{st}$ and $2^{nd}$ containers, thereby enabling any kinks or adhesion between interior walls of the flexible conduit to be removed prior to a separation process such that buoyant materials can travel (e.g., float up) from an inferior chamber to a superior chamber.

Additionally or alternatively, the consumable can include more than 2 containers, a single container, multiple chambers, a single chamber, or be otherwise suitably configured.

In a first example (e.g., as shown in FIG. 3E), the container has a $1^{st}$ chamber and a $2^{nd}$ chamber, the $2^{nd}$ chamber arranged superior to the $1^{st}$ chamber, where the $1^{st}$ and $2^{nd}$ chambers are separated (e.g., initially during a set of processes of the method 200) by a valve and/or other separation component(s) (e.g., conduit, flexible conduit, conduit interfacing with the valve, etc.). In one use case of such a separation container, the $1^{st}$ chamber initially contains the sample materials (e.g., as deposited through a set of access ports [e.g., Luer lock ports on the $1^{st}$ set of container management subsystems]) and the $2^{nd}$ chamber initially contains (e.g., is pre-filled with) culture media or other fluid (e.g., where the $2^{nd}$ chamber is in the form of a gas-permeable cell culture bag pre-filled with culture media), where the $1^{st}$ and $2^{nd}$ chambers are fluidly coupled through the opening of a valve during one or more processes (e.g., S500, once buoyant particles are bound to target material, etc.) of the method 200. Additionally or alternatively, materials can all be added to 1 of the set of containers (e.g., superior container) until a separation process begins (e.g., wherein all of the materials are mixed in 1 container prior to opening of a valve between containers).

The container and/or its associated chambers are preferably configured with geometrical properties that are configured to maximize and/or optimize a transfer of buoyant particles and any bound materials from one chamber (e.g., the inferior chamber) to another chamber (e.g., the superior chamber). This can include, for instance, any or all of: maximizing a percentage of the buoyant particles that are ultimately transferred from one chamber to another, minimizing a percentage the remaining sample (e.g., non-buoyant and non-buoyant-bound particles) that is transferred from the chamber, achieving a uniform and/or nearly uniform distribution of buoyant particles in the chamber that they are transferred to (e.g., minimizing a buildup of buoyant particles in a particular sub-region), and/or otherwise maximizing and/or optimizing this transfer. Additionally or alternatively, the geometrical properties can further function to minimize breakage of buoyant particles (e.g., glass buoyant particles) by gently guiding the particles (and/or preventing direct collisions of buoyant particles with interior walls of containers) and/or otherwise confer benefits to the system and/or method.

These geometrical properties preferably include a variation in diameter of each of the containers, further preferably a variation in diameter that achieves a sloped and/or curved profile of the rigid containers as they approach a location between the containers (e.g., approach a valve, approach a flexible conduit, etc.), such as that shown in any or all of: FIGS. 3E-3G, 3K-3M, 4-8, 13A-13B, and 15A-15B. The slope can be straight in profile (a.k.a. linear slope) (e.g., as shown in FIGS. 13A-13B, as shown in FIG. 6, etc.), curved in profile (e.g., as shown in FIG. 7, as shown in FIG. 8, etc.), a combination of curved and straight, and/or otherwise suitably configured.

In some examples, for instance, during or after a spin process (e.g., light centrifugation with the $2^{nd}$ container management subsystem), a stream of buoyant particles is formed—the pitch (a.k.a. steepness) of the sloped container(s) can facilitate guiding that stream between containers (e.g., preventing a tail of buoyant particles from being left behind, preventing sticking of buoyant particles to interior walls near the spout, etc.). Additionally, the narrowing of the superior container can function to retain buoyant particles (e.g., once they have traveled into the superior container).

The angle (e.g., single angle, average or otherwise aggregated angle, etc.) of the slope (e.g., as depicted in FIG. 13A) can have any suitable value or values, such as, but not limited to: between 30-60 degrees, between 45-90 degrees, between 30-45 degrees, between 20-60 degrees, and/or between any other ranges or range endpoints defined within any of these values.

Each container can be symmetric about a central axis (e.g., as shown in FIGS. 13A-13B), asymmetric about a central axis (e.g., as shown in FIG. 8), and/or can be otherwise shaped.

The slope angle can differ between containers (e.g., as shown in FIGS. 13A-13B), be the same among containers, and/or be otherwise suitably configured. Additionally or alternatively, any other features (e.g., shape, size, etc.) can vary between containers.

In a set of variations (e.g., as shown in FIGS. 3E-3G and 3K-3M, as shown in FIG. 4, as shown in FIG. 5, etc.), for instance, a profile of the inferior container is configured with sloped and/or curved sides leading from a superior region of the inferior container to an inferior region of the superior container, such as with a frustoconical and/or substantially frustoconical shape (e.g., with curved sides, with asymmetric sides, with asymmetric curved sides, etc.), where the decreasing diameter with increasing height guides the buoyant particles from the inferior chamber to the superior chamber (e.g., through a passageway connecting the chambers when a valve or other component is arranged in an open configuration).

Additionally or alternatively, the inferior chamber can have one or more straight sides, sloped sides that increase in diameter with height, and/or any other suitable geometry.

In some examples (e.g., as shown in FIG. 5, as shown in FIG. 6, as shown in FIG. 8), the consumable has an asymmetric profile with one portion/region (e.g., side) of the inferior container having a steeper slope (e.g., average slope) than a slope of the other portion/region (e.g., side). This can function to maximize a transfer and/or ease of transfer of buoyant particles to the superior chamber (e.g., when a valve is in an open configuration) when the container is being spun about an offset axis, such as in a $2^{nd}$ container management subsystem (e.g., as described below). In examples, for instance, the steeper slope can function to guide buoyant particles more easily (e.g., in the presence of centripetal force from rotation of the container) from the inferior container to the superior container during a rotation motion (e.g., spin) of the $2^{nd}$ container management subsystem. This can prevent, for instance, buoyant particles from becoming stuck in the passageway between chambers, enable buoyant particles to be deposited into the superior chamber in a relatively uniform fashion, and/or otherwise optimize the transfer of buoyant particles from the inferior chamber to the superior chamber. Additionally or alternatively, the connection between the inferior and superior chambers can be angled (e.g., non-vertical as shown in FIG. 8) to further assist in guiding materials from the inferior chamber to the superior chamber (e.g., upon opening of a valve arranged between the chambers).

In other examples (e.g., as shown in FIG. 4, as shown in FIG. 8), the slopes can be symmetric. In a particular specific example, the transfer of particles in such a container (and/or in any other container such as an asymmetric container) can be optimized and/or made more efficient through spin protocols of the $2^{nd}$ container management subsystem, such as a reversal of spin direction (e.g., partway through the total spin duration).

In yet other examples (e.g., as shown in FIGS. 13A-13B), each of the superior and inferior containers is symmetric about a central axis, but with one container having a more severe pitch (e.g., inferior container) than the other container. In the particular example shown in FIGS. 13A-13B, for instance, the inferior container has a more significant slope (aka smaller angle) than the superior container, thereby helping guide the buoyant particles to the superior container and then retain the buoyant particles in the superior container.

One or more containers (e.g., the superior container) is preferably configured with a rounded shape, and further preferably a spherical shape (e.g., with a circular profile) and/or ovoid shape (with an ovular profile), which functions to produce a maximal gravitational force at the location of the channel between the inferior chamber and the superior chamber, thereby encouraging the transfer of buoyant particles from the inferior chamber to the superior chamber (e.g., during a spin of the container in the $2^{nd}$ container management subsystem). Additionally or alternatively, the inferior chamber can have such a shape, the superior chamber can have any suitable shape(s) (e.g., asymmetric sloped regions as defined for the inferior chamber, symmetric slopes, etc.), and/or the inferior chamber can be otherwise suitably shaped.

The consumable further preferably includes a housing (e.g., as shown in FIGS. 15A-15B), where the housing functions to partially or wholly enclose the containers throughout any or all of the method 200. Additionally or alternatively, the housing can function to: support and/or define one or more valves (e.g., as described below), allow interfacing (e.g., coupling, optimal coupling, etc.) of the container(s) with the automated instrument, protecting one or more flexible conduits (and/or flexible containers such as in embodiments using bag-based containers), and/or otherwise confer any other functions.

In a preferred set of variants (e.g., as shown in FIGS. 15A-15B), the housing includes a rigid shell which functions to protect and enable selective connection of the containers with the automated instrument, as well as enable manipulation of the containers within the automated instrument.

Additionally or alternatively, the housing can be otherwise configured.

3.3 System: Valve and/or Conduit(s)

The consumable preferably includes a valve and/or other component configured to selectively provide passage of materials between chambers. The valve can be passively activated (e.g., naturally opened during spinning of the container by the $2^{nd}$ container management subsystem), actively activated (e.g., through opening and/or closing of the valve by an actuator or other component of the automated instrument such as according to a protocol), and/or any combination.

The valve can optionally be part of and/or fixed to the housing, which can further function to ensure that the valve is in the proper configuration at each of the container management subsystems (e.g., closed for mixing at the $1^{st}$ container management subsystem, open for separation at the $2^{nd}$ container management subsystem, etc.).

Additionally or alternatively, the valve can be otherwise suitably configured.

The valve preferably interfaces with one or more conduits (e.g., tubes, hoses, cylinders, spouts defined by containers, etc.) (e.g., as described above), wherein the valve enables connection between containers to be selectively enabled (and disabled) through the conduit(s). The valve can be external to the conduit(s) (e.g., operating on exterior walls of the conduit); internal to the conduit(s) (e.g., operating on interior walls of the conduit, operating at an interior space of the conduit, etc.); and/or any combination.

Alternatively, the valves can be used in absence of a conduit. In some variants, for instance, a valve is arranged in one or more of the containers (e.g., in or proximal to a spout of one or more containers).

In a preferred set of variants (e.g., as shown in FIGS. 15A-15B), the valve is arranged external to the container(s) and a deformable conduit connecting the containers such that the valve selectively obstructs flow through the flexible conduit by decreasing its diameter, such as through pinching, twisting, and/or otherwise decreasing the conduit diameter (e.g., to a value below a predetermined threshold, to a value of approximately zero or zero, etc.). In examples (e.g., as shown in FIGS. 13A-13B, as shown in FIGS. 14A-14B, etc.), a set of valve pieces (e.g., clamps) can be rotated relative to each other (e.g., as shown in FIGS. 14A-14B), wherein rotation of the valve pieces in a particular direction squeezes the flexible conduit (decreasing its diameter), and rotation of the valve pieces in the opposing direction allows the conduit to have its full diameter. Additionally or alternatively, the valve pieces can be translated (e.g., pressed together) to restrict flow, or otherwise manipulated to restrict and open flow.

The valve can optionally define one or more levers and/or tabs (e.g., as shown in FIGS. 14A-14B), which can function to: enable a change in operation of the valve (e.g., moving lever clockwise or counterclockwise changes radius of interior aperture of lever); enable selective coupling of the housing with the automated instrument; show which state the valve is being operated in; and/or otherwise suitably function.

In an example shown in FIGS. 14A-14B, the valve includes an external valve having multiple valve pieces, where rotation of the pieces relative to each other changes a diameter of an opening formed by the pieces, thereby either pinching (e.g., restricting, closing, etc.) a conduit arranged in the opening, or releasing (e.g., expanding to a full unfurled diameter) the conduit arranged in the opening. In the particular example shown in FIG. 14B, the distance from a central axis (through a center of the conduit) to a first end ("A") of a curved opening differs from the distance from the central axis to a second end ("B") of the curved opening, where this difference in distance causes a change in the size (e.g., diameter) of the opening formed between the pieces. For instance, as shown in FIG. 14B, since "A" is longer than "B," when the $1^{st}$ valve piece is rotated counterclockwise, portions of the $2^{nd}$ valve piece are driven inward, pinching the conduit closed (e.g., as shown in FIG. 13B). Additionally, the change in position of the lever during rotation can be used to selectively interface with the automated instrument (e.g., as described above and/or below).

In alternative examples, the valve can be a single piece, the valve pieces can translate relative to each other, the valve pieces can change height as they rotate, and/or the valve can be otherwise suitably operated.

In some variants, in order to connect (e.g., lock) the housing/consumable with the automated instrument, the levers need to be in a certain configuration, thereby ensuring that the valve is in the proper state for that particular process of the automated instrument. This can function as a fail-safe mechanism (e.g., such that the user does not attempt to do a separation process with the valve closed, such that the user does not attempt to do a mixing process with the valve open, etc.).

Figure 10:
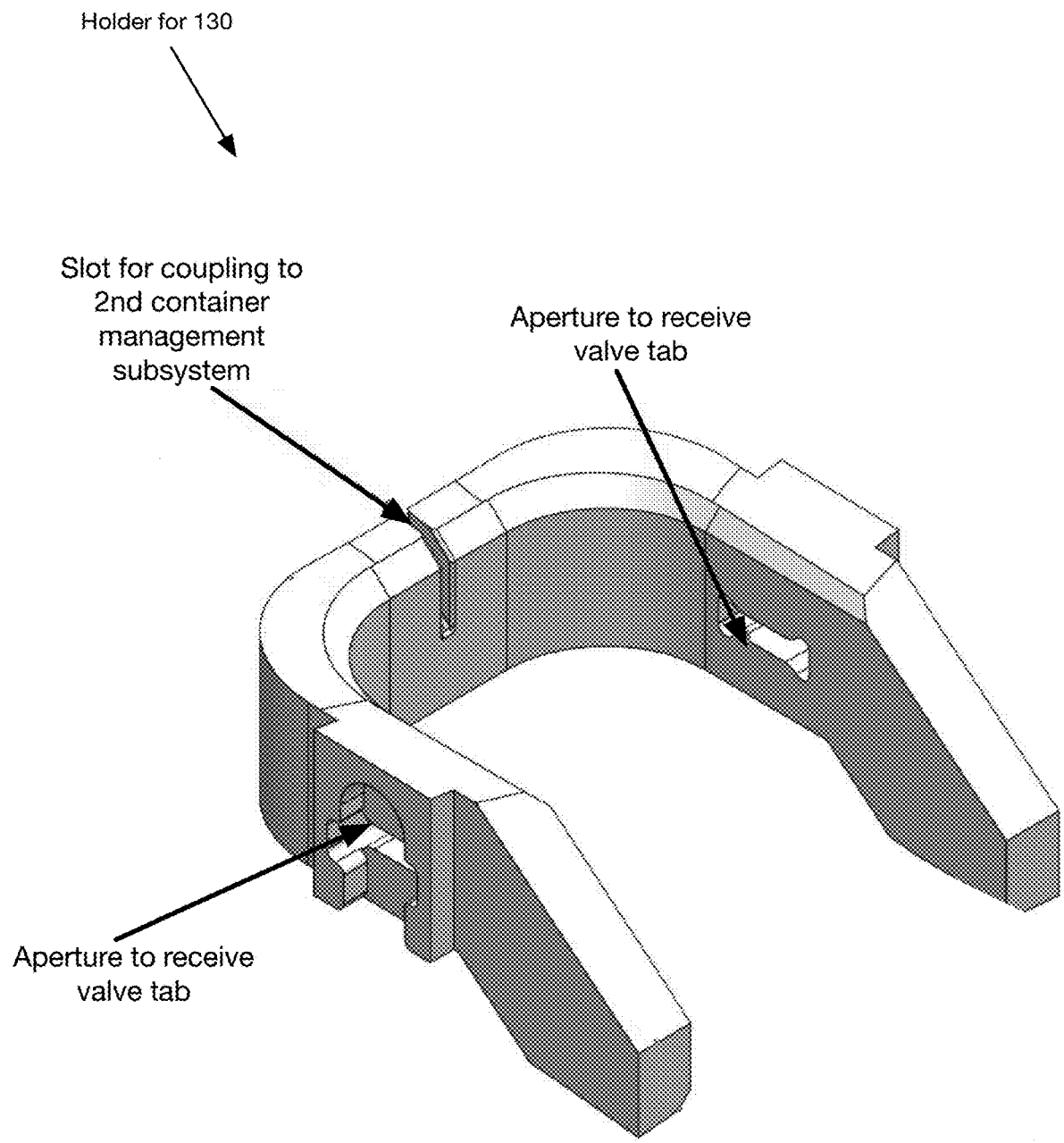
FIG. 10 depicts a variant of a mixing arm for use in the $2^{nd}$ processing subsystem.
Figure 11:
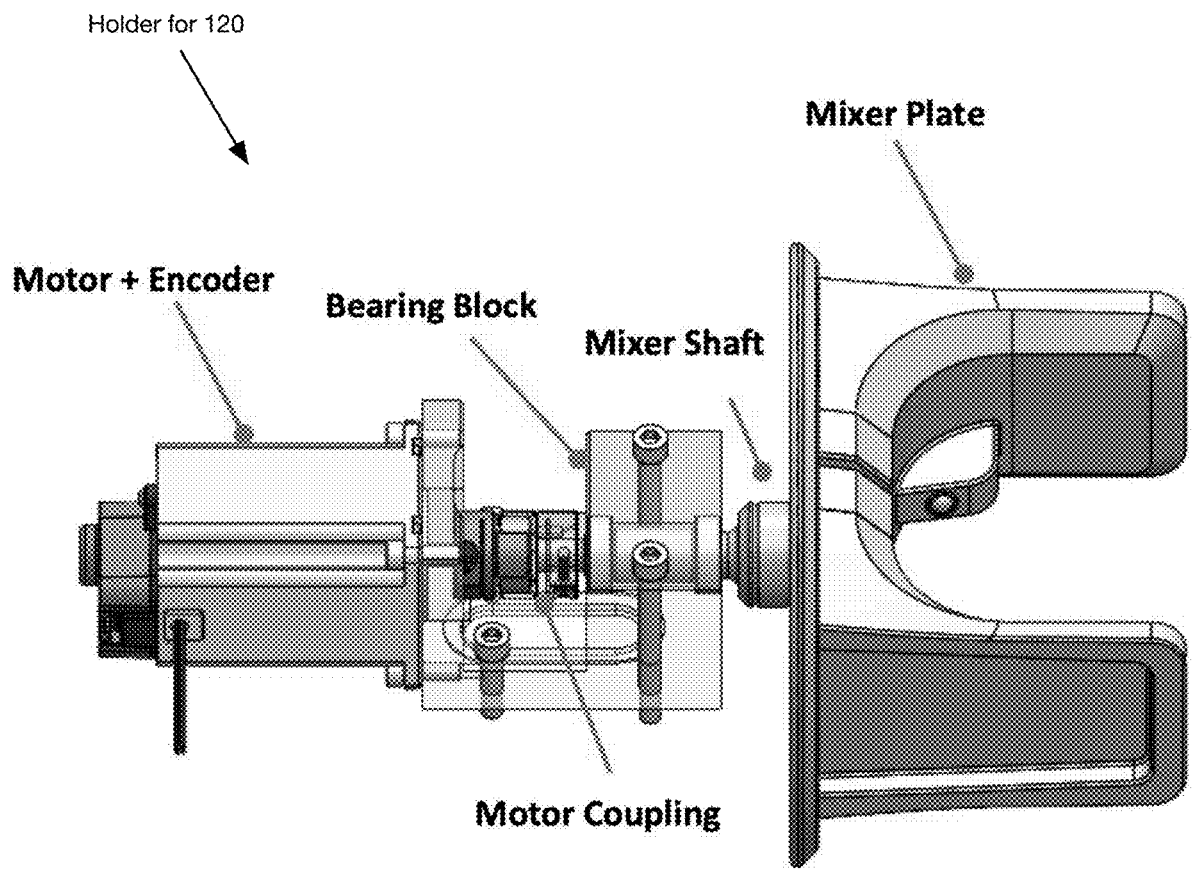
FIG. 11 depicts a variant of a mixing arm for use in the $1^{st}$ processing subsystem.
Figure 12A:
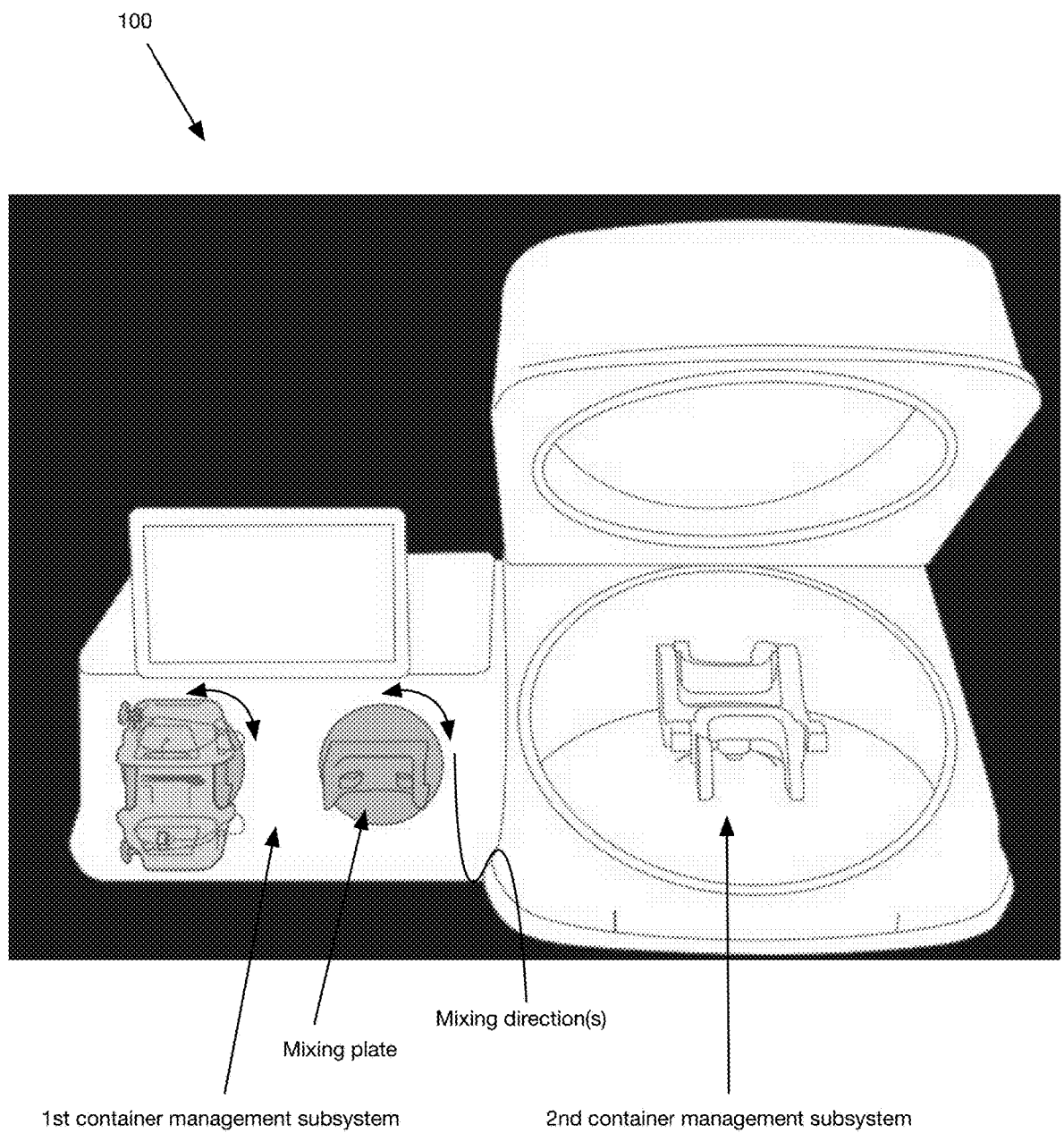
FIGS. 12A-12E depict a variant of the automated instrument and an interfacing with a consumable housing at a $1^{st}$ processing subsystem of the automated instrument.
Figure 12B:
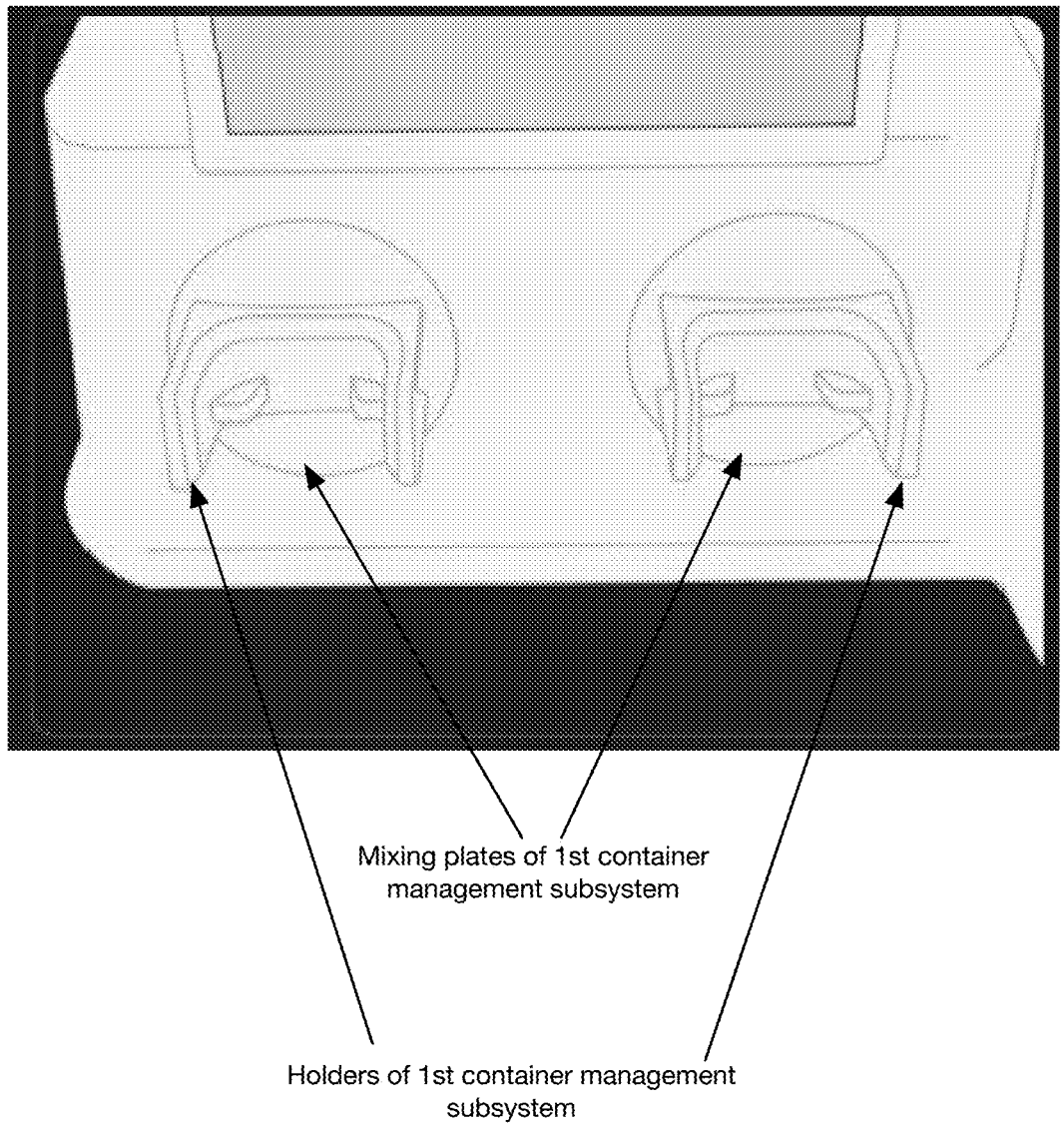
Figure 12C:
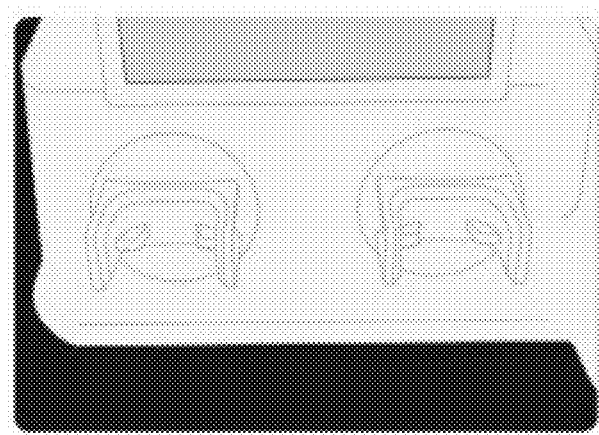
Figure 12D:
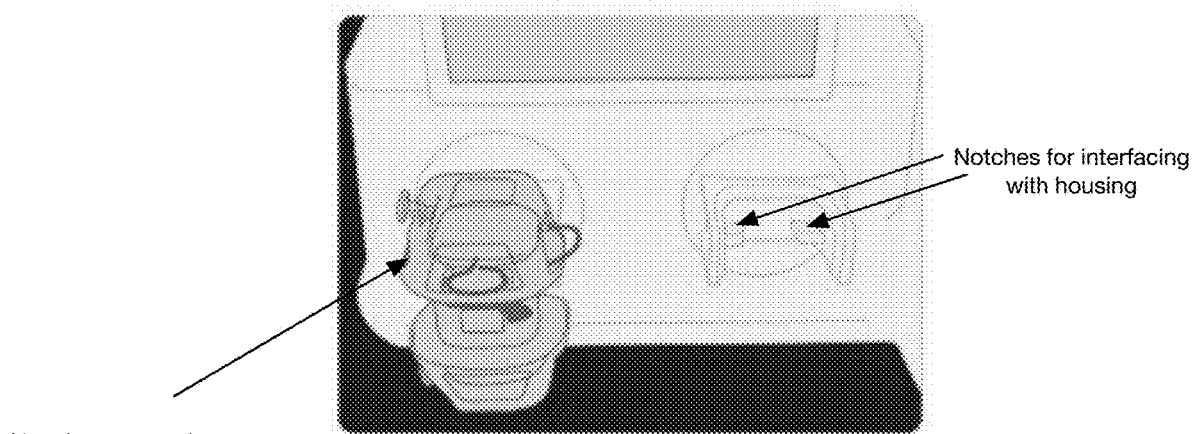
Figure 12E:
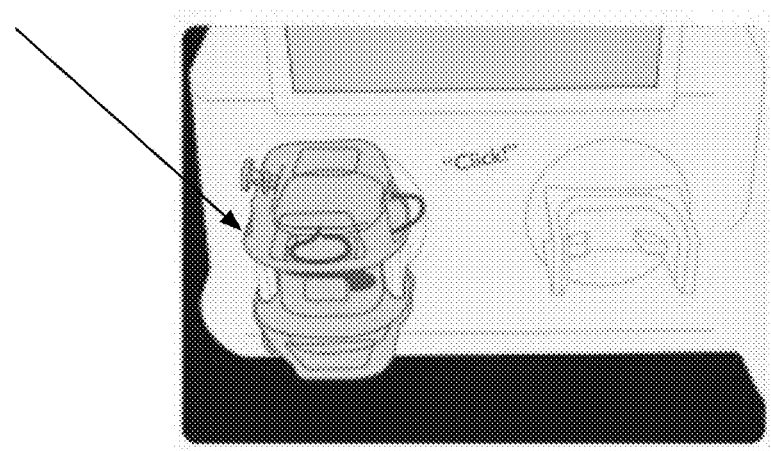

In a particular set of examples (e.g., as shown in FIGS. 14A-14B), the lever rotates with the valve, such that the lever protrudes from a set of slots in the housing when the valve is in a first configuration (e.g., open, closed, etc.), and does not protrude (e.g., recedes behind) from the set of slots when the valve is in a second configuration (e.g., closed, open, etc.), wherein container management subsystems of the automated instrument are accordingly configured to accept the housing based on this state of the lever. For instance, in an event that the lever recedes when the valve is closed, the $1^{st}$ container management subsystem can be configured with protrusions that engage in the slots such that the housing can only be coupled with the $1^{st}$ container management subsystem when the valve is in a closed configuration (e.g., as shown in FIG. 11, as shown in the "click" of FIG. 12E, etc.). And in an event that the lever protrudes when the valve is open, the $2^{nd}$ container management subsystem can be configured with a set of apertures (e.g., as shown in FIG. 10) such that the $2^{nd}$ container management subsystem can only receive and connect with the housing when the valve is in an open configuration. Alternatively, the container management subsystems can be configured in the opposite way, the lever can be otherwise configured, and/or the system can be otherwise suitably configured.

In alternate embodiments, the system can include a valve that is configured to open on its own during a particular process and/or when experiencing a certain set of conditions (e.g., force, particular multiple of gravitational [G] force, speed, orientation, etc.). The valve is preferably configured to open during or immediately prior to a separation process (e.g., during processing with the $2^{nd}$ container management subsystem), but can additionally or alternatively be configured to close at one or more times and/or conditions (e.g., once buoyant particles have traveled to a superior container, once separation has completed, based on a temporal condition such as a threshold time being exceeded, centrifugally-activated, based on an angle threshold being met of a swinging bucket in the $2^{nd}$ container management subsystem, etc.), open and/or close based on automated actuation and/or activation of a tool (e.g., robotic arm, magnet, etc.) in the automated instrument, and/or the valve(s) can be otherwise suitably activated.

In examples, the valve is arranged within a conduit and/or portion of one or more rigid containers (e.g., within a spout) and can transition from a closed to an open configuration once a threshold force (e.g., multiple of G-force, between 1-20 times G-force, between 5-30 times G-force, etc.) is experienced by the valve (e.g., during swinging bucket centrifugation in the $2^{nd}$ container management subsystem). In a particular example, the valve includes a spring and mass, where the threshold force causes and mass to depress the spring and open the valve, allowing fluid flow. Additionally or alternatively, the valve can include any other suitable components, such as a duckbill component (e.g., duckbill valve), stoppers, floats, and/or any other components.

The valve can be manually operated (e.g., by a user), operated in an automated fashion (e.g., actuated by the automated instrument), controlled in another way, and/or controlled in any combination of ways.

Additionally or alternatively, the valve can be otherwise suitably configured.

3.4 System: Container Management Subsystems 120 and 130

The automated instrument preferably includes a set of container management subsystems, which function to manipulate the set of containers (e.g., according to a protocol, according to a protocol specific to the set of materials, etc.), wherein manipulation of the containers functions to execute and/or facilitate processing (e.g., separation, isolation, collection, mixing, etc.) of the materials. The set of container management subsystems preferably includes multiple container management subsystems, which can have the same functionalities, different functionalities, and/or any combination of functionalities. Alternatively, the set of container management subsystems can include a single container management subsystem.

Each of the container management subsystems preferably acts on (e.g., manipulates, moves, rotates, etc.) all containers of the consumable. Alternatively, any or all of the container management subsystems can act on a single container or subset of containers, or on any other part(s) of the system.

In a preferred set of variations (e.g., as shown in FIGS. 3A-3C, 3H-3J), the set of container management subsystems includes a $1^{st}$ container management subsystem and a $2^{nd}$ container management subsystem, where the $1^{st}$ and $2^{nd}$ container management subsystems are preferably each configured to manipulate (e.g., translate, rotate, interface with, add and/or remove materials to and from, etc.) the set of containers (aka consumable) and/or housing (e.g., in an automated fashion, in a semi-automated fashion, etc.). Additionally or alternatively, the set of container management subsystems can include additional container management subsystems, a subset of these container management subsystems, and/or any other container management components.

The $1^{st}$ container management subsystem is preferably configured for any or all of: the addition and/or removal of materials, the mixing (e.g., rotational mixing, end-over-end mixing, etc.) of materials, the transfer of containers from the $1^{st}$ container management subsystem to the $2^{nd}$ container management subsystem, and/or for any other functions.

The $1^{st}$ container management subsystem (and/or any other container management subsystems) is preferably operated according to a protocol (e.g., customizable to and/or by a user, predetermined, dynamically determined and/or adjusted, etc.), such as a mixing (e.g., end-over-end mixing, modified end-over-end mixing, etc.) protocol. The protocol can prescribe any number of parameters and parameter values, such as, but not limited to: speeds (e.g., rotational speed); angles (e.g., range of angles that mixing plate rotates to, maximum angle of rotation, start angle and/or end angle and/or intermediate angles, etc.); accelerations (e.g., rotational accelerations, to prescribe vortexing, to prescribe shaking, etc.); temporal parameters (e.g., for pauses, when to stop, to prescribe moving to a certain angle and then stopping, etc.); and/or any other parameters.

In some variants, a concentration of cells (or other target materials) and/or total volume of materials being separate (e.g., bulk volume, sample volume, etc.) can affect any or all parameters. For instance, in an event that there is a small amount of sample (e.g., target material, bulk volume, etc.) present, a shorter or less intense (e.g., slower speed, smaller angle range, etc.) mixing protocol can be implemented to prevent the small amount of sample from coating an interior of the container and not optimally separating.

In a preferred set of variants (e.g., as shown in FIGS. 12A-12E, as shown in FIG. 11), for instance, the $1^{st}$ container management subsystem is configured to mix (e.g., through end-over-end mixing, through modified end-over-end mixing, etc.) the contents of one or more containers of the consumable through rotation of the consumable. Additionally, the $1^{st}$ container management subsystem can translate or otherwise process (e.g., heat, cool, add materials to, extract materials from, etc.) the contents of the container(s). As such, the $1^{st}$ container management subsystem preferably includes a fixture (e.g., holder) that holds (e.g., secures) the consumable (e.g., via the housing, via tabs in the housing, via apertures in the housing, etc.) and rotates it (e.g., perpendicular to a central axis of the consumable) according to a protocol (e.g., through a motor with an encoder driving a mixer shaft and plate as shown in FIG. 11). The holder can optionally include or define any number of features, such as apertures (e.g., to couple with the consumable); slots, tabs, prongs, protrusions, clips, screws, or other mechanisms for attaching the holder to a remainder of the automated instrument (e.g., slot in FIG. 10 can couple the holder to the automated instrument and/or maintain orientation of the holder relative to the instrument); and/or any other features. Additionally or alternatively, the $1^{st}$ container management subsystem can do other types of mixing (e.g., spinning about a central axis, centrifugation, etc.) and/or any other processing.

In an example, the $1^{st}$ container management subsystem is configured to perform modified end-over-end mixing of the contents of one or more containers (e.g., superior container, inferior container, etc.). In a particular example, the protocol involves rotating the consumable a first angle amount (e.g., 360 degrees, between 180 and 360 degrees, 270 degrees, greater than 360 degrees, less than 360 degrees, any range in between said values, etc.) in a first direction (e.g., counterclockwise, clockwise, etc.), coming to a stop (e.g., momentarily, for a predetermined duration of time, etc.), and then rotating the consumable by a second angle amount (e.g., same as the first angle amount, different than the first angle amount, etc.) in the opposing direction, effectively forming a pendulum mixer.

Figure 3H:
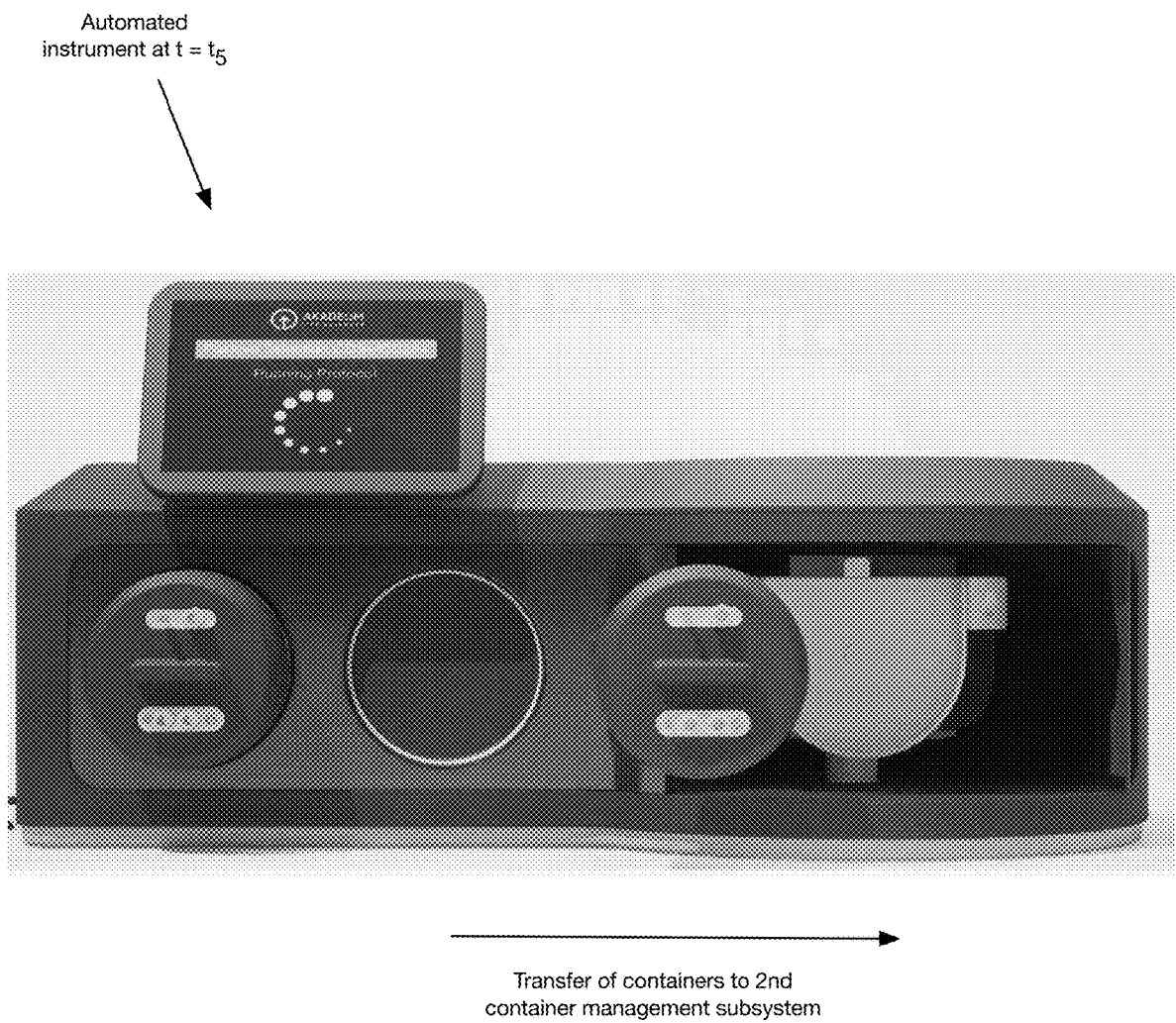
Figure 3I:
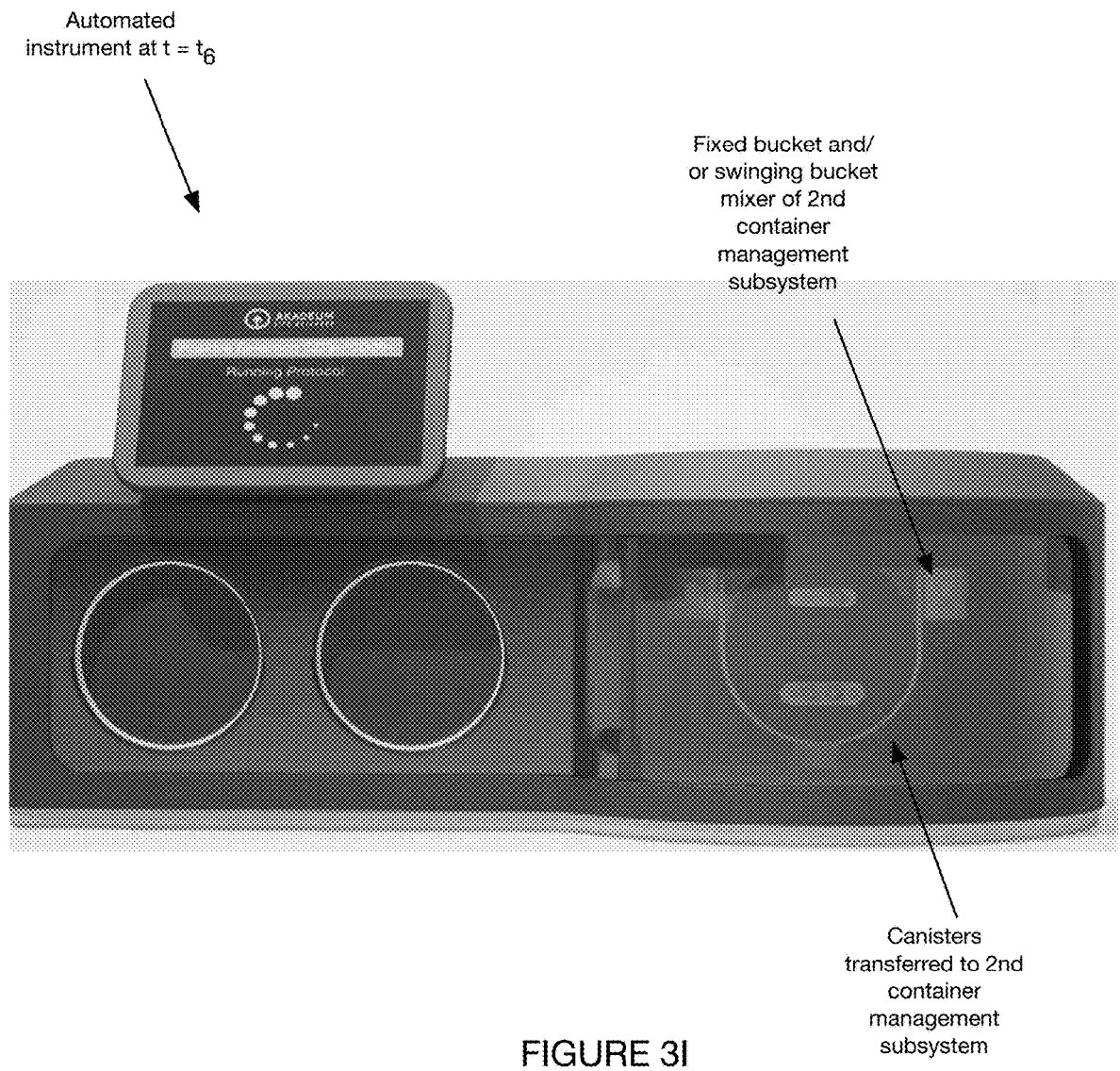
Figure 3J:
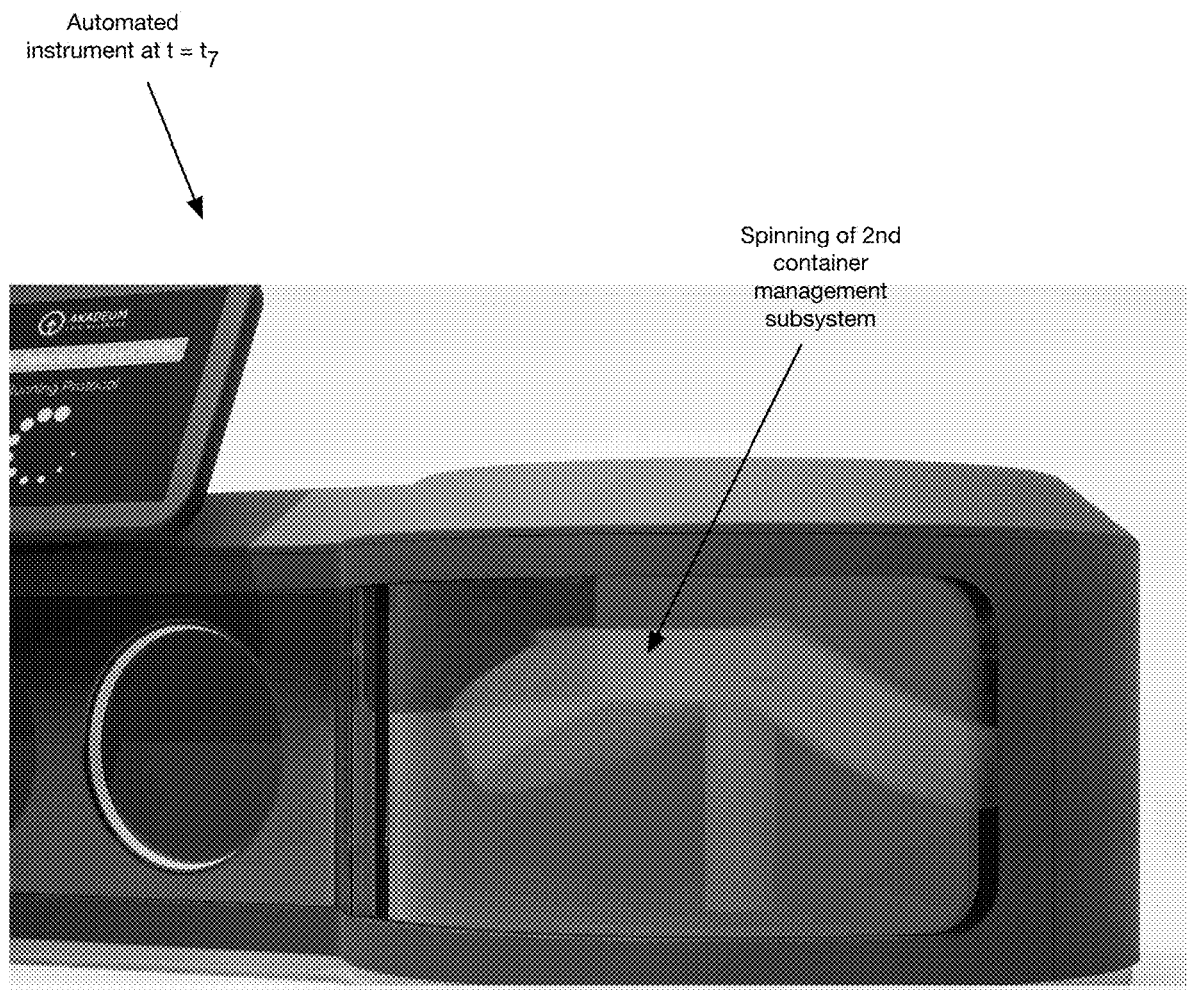
Figure 3K:
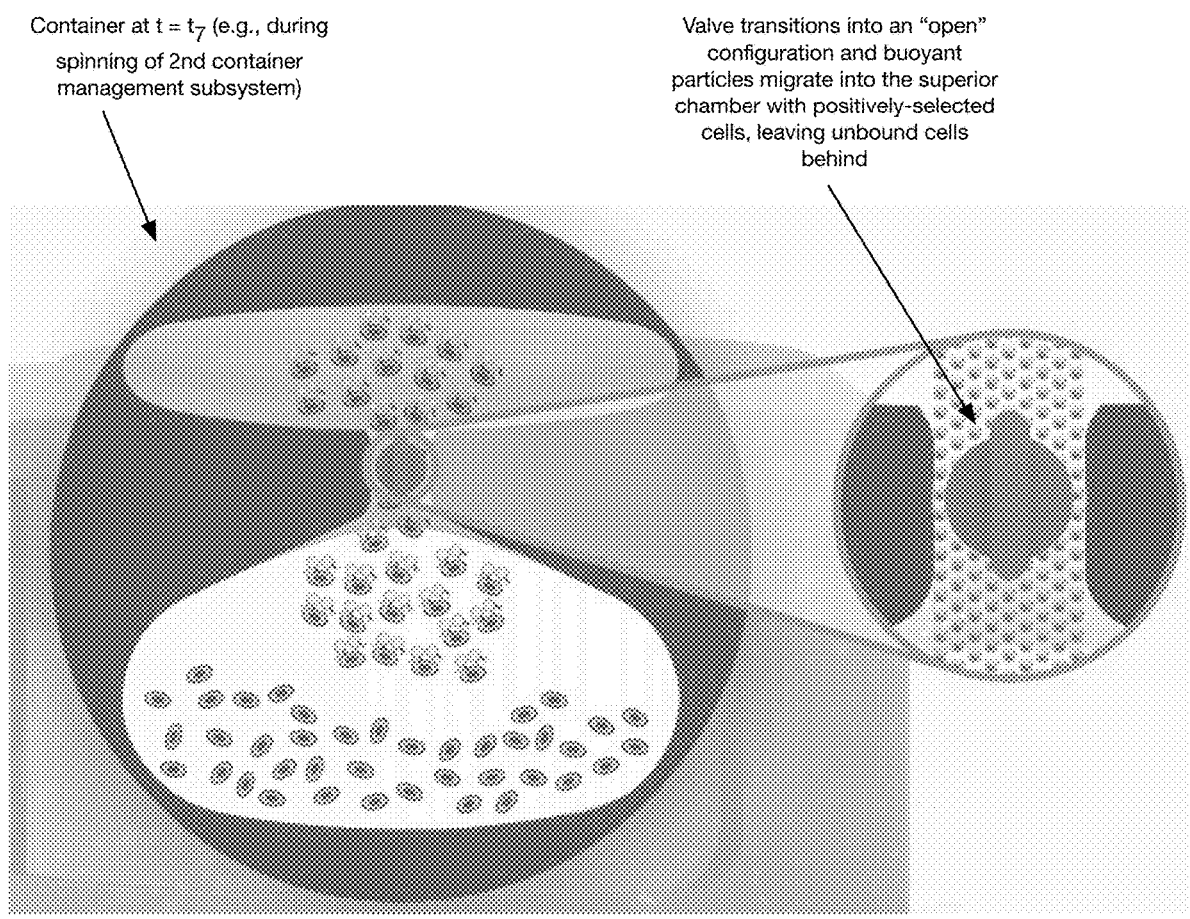
Figure 3L:
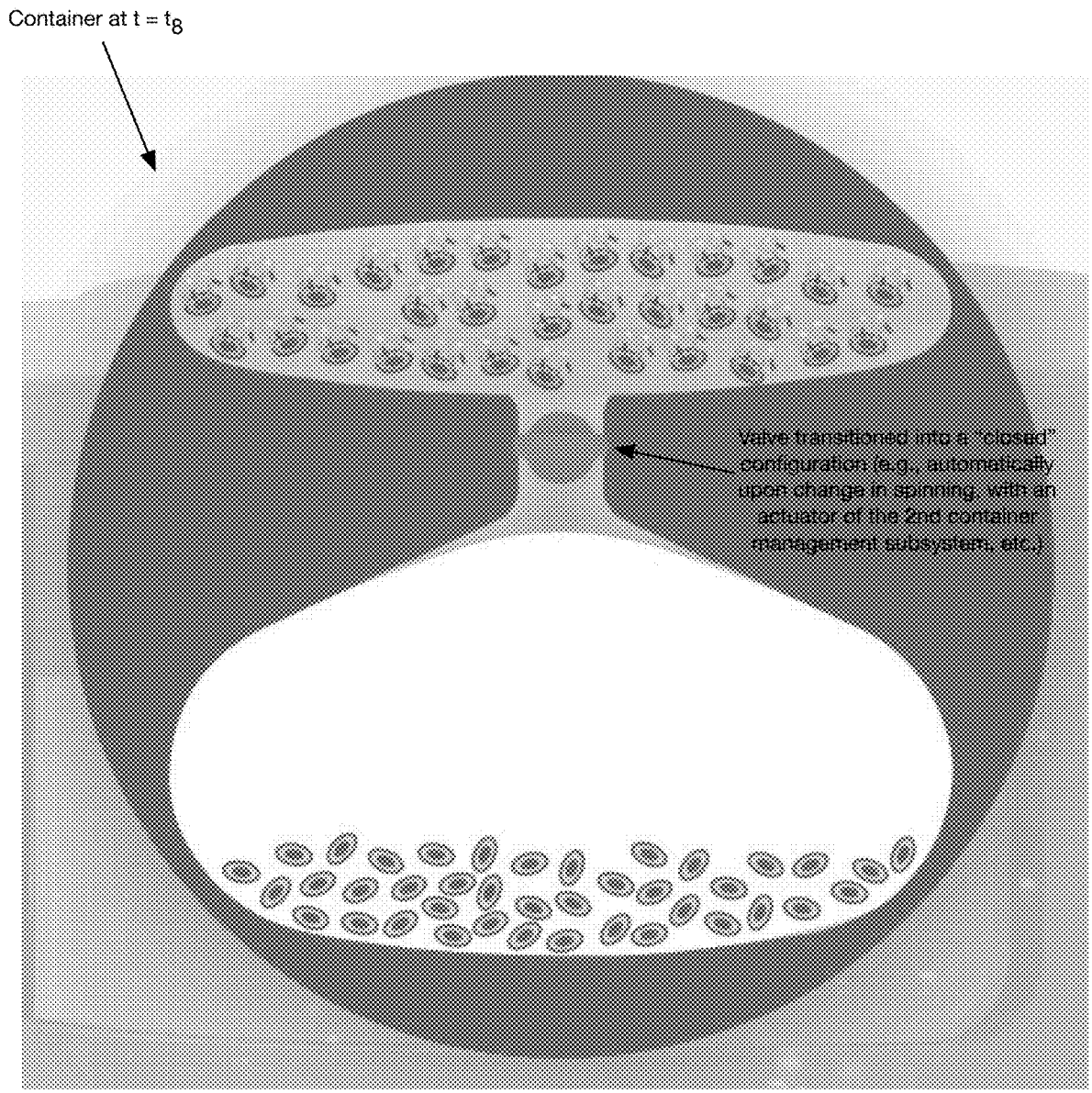
Figure 3M:
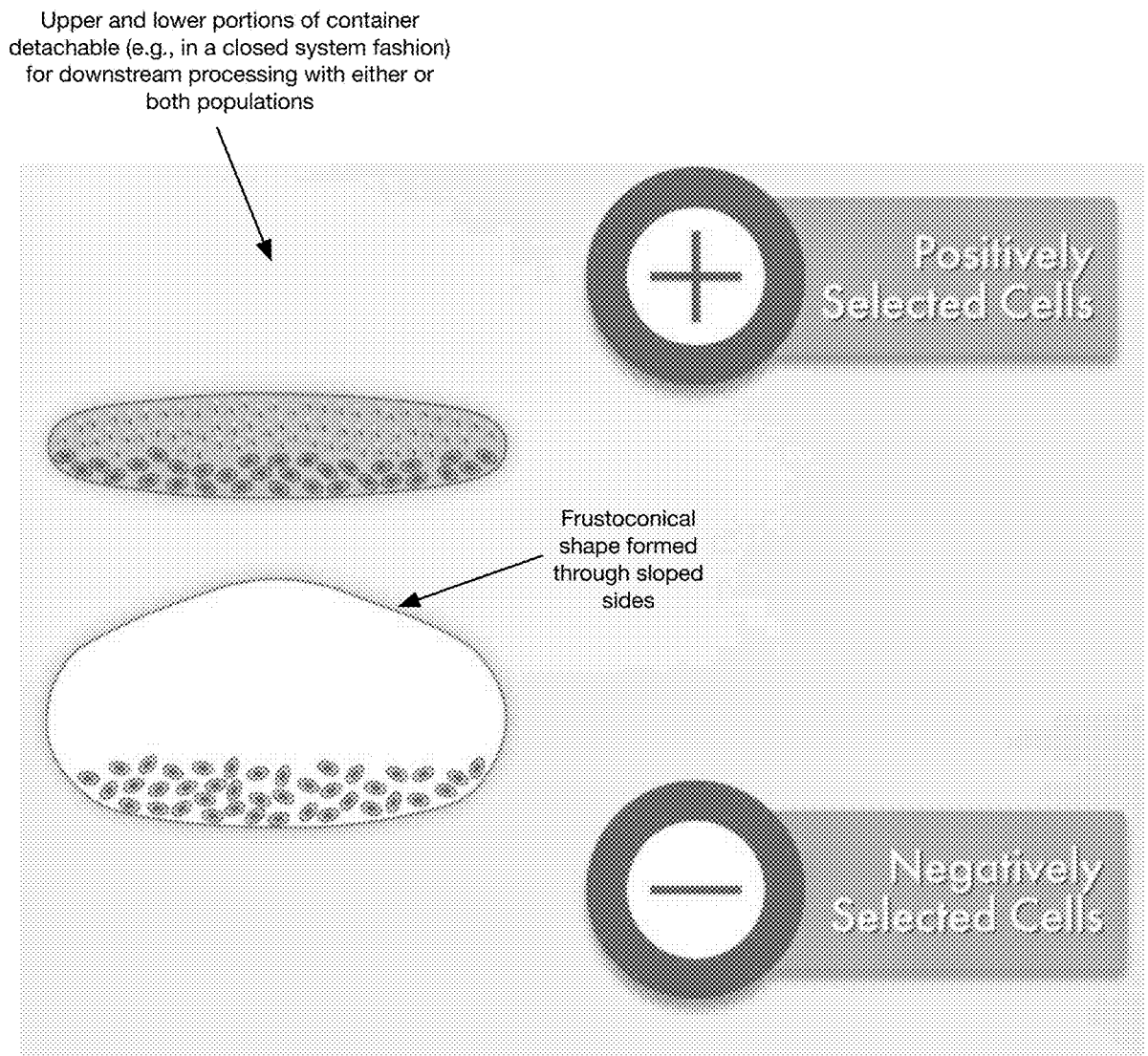

In other variants, the $1^{st}$ container management subsystem includes and/or interfaces with a set of cartridges (e.g., canisters as shown in FIG. 3C) that receive the set of containers, where the $1^{st}$ container management subsystem includes the receiving cavities for the cartridges and associated components (e.g., actuators, motors, wheels, tracks, etc.) for manipulating the set of cartridges. The containers can be empty, pre-filled with any or all of the materials (e.g., pre-filled with culture media at a superior chamber), and/or otherwise configured when received at the $1^{st}$ container management subsystem (e.g., initially in the protocol). The cartridges (e.g., cylindrical canisters) are preferably configured to perform any or all of: receiving the set of containers, holding the set of containers (e.g., in an optimal configuration), rotating the set of containers (e.g., to perform mixing of materials within the chambers and/or within the container, to perform end-over-end mixing, etc.), transiting the set of containers (e.g., between locations of the automated instrument), otherwise processing (e.g., heating, cooling, etc.) materials of the set of containers, and/or performing any other processes. In a set of examples, for instance, the $1^{st}$ container management subsystem includes a set of cylindrical canisters that are configured to rotate (e.g., in an automated fashion, in a semi-automated fashion, according to a rotational protocol, etc.) and thereby perform end-over-end mixing of the container contents. This can function to facilitate, for instance, the bonding of buoyant particles with the associated target material (e.g., in the inferior chamber). Additionally or alternatively, the $1^{st}$ container management subsystem can function to move to and/or be placed in a $2^{nd}$ container management subsystem (e.g., as shown in FIGS. 3H-3J), such as for additional processing.

The chambers of the containers are preferably fluidly isolated from each other (aka valve is closed) throughout a duration of time at which the consumable is at the $1^{st}$ container management subsystem (e.g., within the receiving apertures shown in FIG. 3C), but can alternatively be fluidly connected for any or all of this duration. In examples, for instance, the chambers are only fluidly connected after the canisters of the $1^{st}$ container management subsystem have transferred to the $2^{nd}$ container management subsystem (e.g., and a valve has been released during mixing).

The $2^{nd}$ container management subsystem is preferably configured to enable (e.g., through the opening of a valve) and/or optimize a transfer of materials between chambers (equivalently referred to herein as separation), and further preferably configured to optimize (e.g., in efficiency, in yield, etc.) the transfer of buoyant particles and any materials bound to the buoyant particles from an inferior chamber to a superior chamber. This is preferably enabled through spinning (e.g., gentle spinning, spinning with a G-force significantly less than that of a conventional centrifuge, between 10-150 times G-force, between 25-125 times G-force, between 10-50 times G-force, between 15-100 times G-force, less than 150 times G-force, less than 125 times G-force, less than 100 times G-force, etc.), but can additionally or alternatively be enabled through any other suitable spinning components and/or protocols and/or parameters.

The $2^{nd}$ container management subsystem is preferably operated according to a protocol (e.g., as described above for the $1^{st}$ container management subsystem), which can control any or all parameters of the automated instrument. These can include speeds, angles, accelerations, times, direction of rotation (e.g., clockwise, counterclockwise, etc.), combinations of parameters (e.g., move at a $1^{st}$ speed for a $1^{st}$ time duration and move at a $2^{nd}$ speed for a $2^{nd}$ time duration, etc.), and/or any other parameters (e.g., as described above). The protocol(s) can be predetermined (e.g., and selected by a user), dynamically determined and/or adjusted, determined based on user input (e.g., at a user interface), and/or any combination.

In examples, one or more protocols of the spin subsystem (e.g., for cell separation) prescribe rotational speeds below a predetermined threshold, which can be configured to promote and protect cell health.

The $2^{nd}$ container management subsystem is preferably configured to enable and/or facilitate (e.g., encourage, allow, optimize for, etc.) separation (e.g., longitudinal separation, buoyant separation, etc.) of buoyant particles and any bound target materials from any or all of a remainder of a bulk volume. In preferred variants, the $2^{nd}$ container management subsystem does so through spinning (e.g., centrifuging) the consumable. Additionally or alternatively, the $2^{nd}$ container management subsystem can facilitate separation through a stationary processing of the consumable, through other movement (e.g., translation, rotation, shaking, etc.) of the consumable, through other processing (e.g., heating, cooling, etc.) of the consumable, any combination of processing, and/or any other processing.

Figure 16:
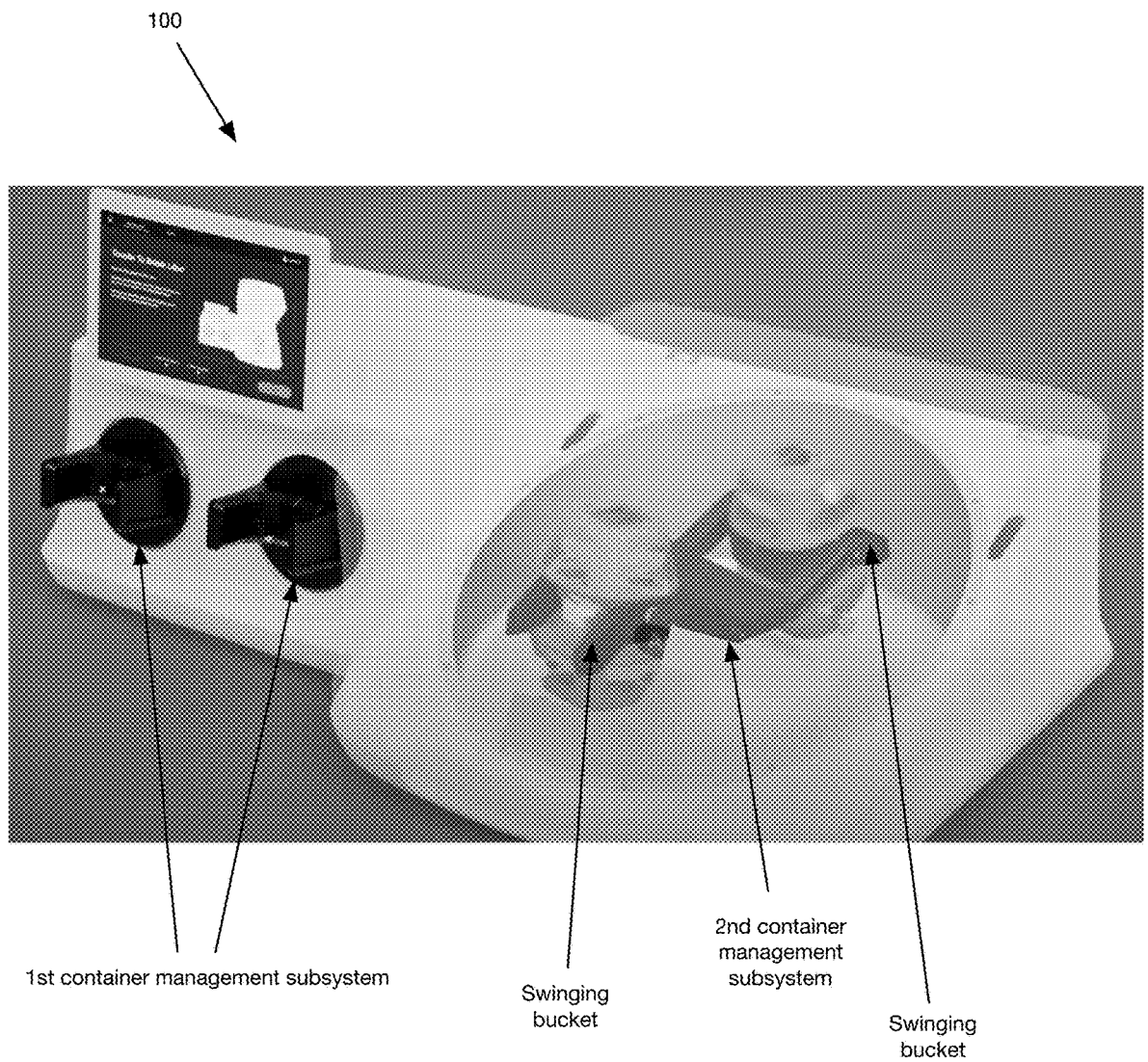
FIG. 16 depicts a variant of the automated instrument.

In a preferred set of variations, for instance, the $2^{nd}$ container management subsystem includes a spin subsystem (e.g., fixed bucket mixer/centrifuge, swinging bucket mixer/centrifuge such as shown in FIG. 16, centrifuge, etc.) configured to facilitate movement (e.g., in addition to the natural vertical movement conferred by buoyant forces) of the buoyant particles to the superior chamber. Additionally or alternatively, any other features can contribute to optimize this transfer, such as, but not limited to: a shape and/or other geometric features of the container (e.g., rounded shape of superior chamber as described above, asymmetric shape of the inferior chamber, etc.), a pre-filling of the superior chamber with fluid, features of the protocol (e.g., speed of spin, angle of spin, etc.), and/or any other features.

In examples, the $2^{nd}$ container management subsystem includes a swinging bucket centrifuge (e.g., that reaches at least a 45-degree-angle/horizontal configuration when spinning).

In alternative examples, the $2^{nd}$ container management subsystem includes a fixed-angle bucket centrifuge.

The spin subsystem can optionally additionally function to open a valve or other separation component arranged between multiple chambers of the container. In examples, for instance, the spin subsystem is configured to produce at least a minimum force (e.g., G-force) needed to open a passively activated valve. Additionally or alternatively, the valve can be opened by another component (e.g., actuator, electronic component, magnetic component, etc.) of the automated subsystem, and/or otherwise suitably opened. The spin subsystem and/or other components of the automated instrument can optionally further be configured to close a valve (e.g., once buoyant particles have transferred to the superior chamber), such as based on an optimized spin protocol (e.g., which enables passive closing of the valve at an optimal time) and/or implementation of components (e.g., actuators, electronic components, magnetic components, sensors, etc.) configured for closing the valve.

The $2^{nd}$ container management subsystem can include any number of fixtures (e.g., holders) configured to hold/connect to the consumable (e.g., via the housing) (e.g., as shown in FIG. 10).

In specific examples, the spin subsystem includes a bucket mixer, where the bucket can be (e.g., for all protocols, depending on protocol type, etc.) any or all of: fixed (e.g., in a vertical arrangement, in a horizontal arrangement, at a predetermined angle [e.g., 45-degrees, between 30-60 degrees, etc.], etc.), swinging (e.g., with a variable angle, with a variable angle up to a maximum angle of 45 degrees relative to vertical, etc.), and/or any combination.

Additionally or alternatively, the $2^{nd}$ container management subsystem can include any other components and/or be otherwise suitably configured.

3.5 System: User Interface Subsystem 140

The automated instrument can optionally include a user interface subsystem, wherein the user interface subsystem can include any or all of: a display (e.g., to receive selection of a protocol or other inputs from a user, to display information regarding a protocol to a user, etc.), a scanner (e.g., to scan a barcode associated with a container or other vessel of materials where the barcode is configured to convey a particular protocol to be implemented by the automated instrument, etc.), and/or any other suitable components (e.g., mouse, touchpad, keyboard, tube sealer, tube welder, etc.).

The system preferably interfaces with and/or includes the set of buoyant particles, such as any or all of those described in U.S. application Ser. No. 16/004,874, filed 11 Jun. 2018, U.S. application Ser. No. 14/969,446, filed 15 Dec. 2015, U.S. application Ser. No. 17/679,688, filed 24 Feb. 2022, and U.S. application Ser. No. 17/896,800, filed 26 Aug. 2022, and U.S. application Ser. No. 18/114,130, filed 24 Feb. 2023, each of which is incorporated herein in its entirety by this reference. The buoyant particles are preferably characterized by a density less than that of the other particles in the set of materials (and/or an average density of bulk fluid in the sample), such that the buoyant particles are configured to float at a surface of the fluids it is immersed in. The buoyant particles are further preferably configured to be functionalized with factors (e.g., with antibodies, moieties, etc.) configured to facilitate binding of the buoyant particles with particular target particles of the set of materials. Additionally or alternatively, the buoyant particles can be otherwise suitably configured.

Additionally or alternatively, the system 100 can include and/or interface with any other suitable components.

4. Method 200

As shown in FIG. 2, a method 200 for partially or fully automated, buoyancy-assisted separation includes manipulating the set of containers and/or processing the set of materials at a $1^{st}$ container management subsystem S300 and manipulating the set of containers and/or processing the set of materials at a $2^{nd}$ container management subsystem S500. Additionally or alternatively, the method 200 can include any or all of: receiving a set of materials at a set of containers S100; receiving the set of containers at a $1^{st}$ container management subsystem S200; receiving the set of containers at a $2^{nd}$ container management subsystem S400; removing the set of containers and/or the set of materials from the automated instrument S600; and/or any other suitable processes.

Further additionally or alternatively, the method can include and/or interface with any or all of the processes as described in: U.S. application Ser. No. 16/004,874, filed 11 Jun. 2018, U.S. application Ser. No. 14/969,446, filed 15 Dec. 2015, U.S. application Ser. No. 17/679,688, filed 24 Feb. 2022, and U.S. application Ser. No. 17/896,800, filed 26 Aug. 2022, and U.S. application Ser. No. 18/114,130, filed 24 Feb. 2023, each of which is incorporated in its entirety by this reference, or any other suitable processes performed in any suitable order. The method 200 can be performed with a system as described above and/or any other suitable system.

The method 200 preferably functions to enable separation of materials within a sample in an automated (e.g., fully automated) or semi-automated fashion, but can additionally or alternatively perform any other suitable functions.

The method 200 can optionally include receiving a set of materials at a set of containers S100, which functions to receive, in a sterile (e.g., closed-system) fashion, any or all of the particles, buffers, media, and/or other materials to be processed in the method 200. Alternatively, any or all of the materials can be pre-filled into the container(s). The materials are preferably deposited into a container through a set of access ports (e.g., Luer lock access port) present on a cartridge of the $1^{st}$ container management subsystem, but can additionally or alternatively be otherwise suitably deposited. The access ports can additionally or alternatively be utilized to remove materials from the container.

S100 is preferably performed initially during the method 200, but can additionally or alternatively be performed at other times during the method 200, and/or at any other suitable times.

The method 200 can optionally include receiving the set of containers at a $1^{st}$ container management subsystem S200, which functions to prepare the containers for processing in subsequent processes of the method 200. S200 can be performed prior to S100, after S100, in absence of S100, and/or at any other time(s). The containers are preferably received at and placed in cartridges (e.g., canisters) of the $1^{st}$ container management subsystem, wherein the cartridges are placed in receiving apertures of the automated instruments, but can additionally or alternatively be otherwise suitably received at the $1^{st}$ container management subsystem.

The method 200 preferably includes manipulating the set of containers and/or processing the set of materials at the $1^{st}$ container management subsystem S300, which functions to initialize, prepare for, and/or perform at least a portion of a separation process utilizing buoyant particles. S300 is preferably performed while chambers of the container are fluidly isolated (e.g., as described above), but any or all of S300 can alternatively be performed while two or more chambers are fluidly coupled. S300 preferably includes rotating the containers (e.g., through rotation of the cartridges) to facilitate mixing (e.g., end-over-end mixing, spinning, etc.) of materials, the mixing of materials configured to facilitate binding of the buoyant particles with their target materials (e.g., increase exposure of the buoyant particles to the target material), but can additionally or alternatively include translating the containers (e.g., through translation of the cartridges) and/or any other processes.

The method 200 can optionally include receiving the set of containers at a $2^{nd}$ container management subsystem S400, which functions to initiate additional processing of the materials (e.g., in S500). S400 is preferably performed through movement (e.g., translation) of the cartridges containing the containers from receiving apertures of the $1^{st}$ container management subsystem to a mixing subsystem (e.g., bucket mixer) of the $2^{nd}$ container management subsystem, but can additionally or alternatively include any other processes. S400 is preferably performed after S300, but can additionally or alternatively be performed at any other suitable time(s).

The method 200 preferably includes manipulating the set of containers and/or processing the set of materials at the $2^{nd}$ container management subsystem S500, which functions to isolate the buoyant particles and any bound materials from a remainder of the set of materials. S500 is preferably performed in response to S400, but can additionally or alternatively be performed at any other suitable times.

S500 can include any or all of: spinning the set of containers, opening and/or closing a valve associated with the set of containers, separating (e.g., permanently separating) the chambers from each other (e.g., through sealing of the connection between chambers once separation has been performed, through permanent closing of the valve, through dividing [e.g., cutting] the container into multiple pieces after separation, etc.), and/or any other processes.

Alternatively, multiple processes (e.g., multiple mixing processes, end-over-end mixing and spinning, mixing and centrifugation, etc.) can be performed at a single location of the automated instrument and/or with a single apparatus (equivalently referred to herein as a single mixing apparatus), which can be configured with: multiple axes of rotation, translation mechanisms, multiple actuators and/or types of actuators, and/or any other component(s).

The method 200 can optionally include removing the set of containers and/or the set of materials from the automated instrument S600, which functions to enable usage and/or further processing of the materials. In examples, S600 can include adding materials to the consumable (e.g., without user intervention, with user intervention, etc.); draining materials from the consumable (e.g., without user intervention, with user intervention, etc.); and/or any other processes. S600 is preferably performed in response to S500, but can additionally or alternatively be performed at any other suitable times. Any or all of S600 can be performed in an automated fashion (e.g., without user intervention), in a semi-automated fashion (e.g., partially automated, with minimal user intervention, etc.), in a non-automated fashion, and/or in any other way(s).

Additionally or alternatively, the method 200 can include any other suitable processes.

5. Variants

In a first variant of the system, the system for assisted buoyant separation of target materials from a gross volume can include any or all of: a first chamber, the first chamber defined by a rigid first container; a second chamber, the second chamber defined by a rigid second container; a deformable conduit arranged between the rigid first container and the rigid second container, the deformable conduit configured to selectively fluidly connect the first and second chambers; a housing including: a valve configured to interface with the deformable conduit, the valve operable in a set of operation modes (a $1^{st}$ mode, wherein in the first mode, the first chamber is fluidly disconnected from the second chamber, and a $2^{nd}$ mode, wherein in the second mode, the first chamber is fluidly connected to the second chamber, etc.); an automated instrument including: a $1^{st}$ processing subsystem (wherein the housing can couple to the $1^{st}$ processing subsystem when the valve is operated in the $1^{st}$ mode, wherein the $1^{st}$ processing subsystem is configured to mix the target materials in the gross volume with a set of buoyant particles, etc.), and a $2^{nd}$ processing subsystem (wherein the housing can couple to the $2^{nd}$ processing subsystem when the valve is operated in the $2^{nd}$ mode, wherein the $2^{nd}$ processing subsystem is configured to separate the target materials from the gross volume with the set of buoyant particles, etc.); and/or any other components.

In a first variant of the method, the method can include: receiving (e.g., from a user via a user interface) and/or retrieving (e.g., from memory) a protocol selection (e.g., human T cell negative selection, human T cell positive selection, etc.); triggering initiation of the protocol; receiving a set of one or more consumables at a 1st mixing subsystem of an automated instrument; receiving and/or automatically adding materials (e.g., media, sample, cells, antibodies, etc.) to one or more chambers of the consumable (e.g., via a set of ports and/or tubing); initiating and performing any or all of a $1^{st}$ mixing process (e.g., end-over-end mixing, modified end-over-end mixing, etc.) for a duration of time (e.g., 10-15 min); optionally adding one or more additional materials (e.g., microbubbles) to one or more chambers; optionally performing additional portions and/or iterations of the $1^{st}$ mixing process (e.g., with the same mixing parameters, with different mixing parameters, etc.) (e.g., for 10-15 minutes); optionally transferring the container (e.g., through actuated elements, in an automated fashion, through manual user intervention, etc.) to a $2^{nd}$ mixing subsystem (e.g., centrifuge, swinging bucket centrifuge, etc.); spinning (e.g., at a lower speed than a traditional centrifuge, at a lower speed than mixing in the $1^{st}$ mixing subsystem, etc.) the container with the $2^{nd}$ mixing subsystem (e.g., for 2-3 min, for a shorter duration than mixing in the $1^{st}$ mixing subsystem, for a longer duration than mixing in the $1^{st}$ mixing subsystem, etc.), which can function to enable separation (e.g., microbubbles and bound materials traveling to the superior chamber, a different in composition between chambers, etc.); optionally draining materials from one or more chambers (e.g., for placement in a bag or other new container); and/or any other processes.

In an alternative variant of the method, the mixing processes are all performed at a single mixing subsystem (e.g., configured to rotate materials in multiple directions/about multiple different axes).

In another variant of the method, the method can include any or all of: receiving, at a $1^{st}$ rigid container: a gross volume including the set of target materials and a set of buoyant particles, the set of buoyant particles configured to bind with the set of target materials; receiving, at a $1^{st}$ processing subsystem of an automated instrument: a housing comprising the $1^{st}$ rigid container, the housing further including a $2^{nd}$ rigid container, a deformable conduit arranged between the $1^{st}$ rigid container and the $2^{nd}$ rigid container, and a valve interfacing with the deformable conduit, wherein the valve selectively enables fluid communication between the $1^{st}$ rigid container and the $2^{nd}$ rigid container via the deformable conduit, and wherein the housing can be coupled with the $1^{st}$ processing subsystem only when the valve is in a closed configuration; operating the $1^{st}$ processing subsystem, comprising mixing contents of the $1^{st}$ rigid container, thereby facilitating binding of the set of target materials with the set of buoyant particles; receiving the housing, at a $2^{nd}$ processing subsystem of the automated instrument, wherein the housing can be coupled with the $2^{nd}$ processing subsystem only when the valve is in an open configuration; and operating the $2^{nd}$ processing subsystem, including mixing contents of the $1^{st}$ and $2^{nd}$ rigid containers, thereby facilitating separation of the target material from a remainder of the gross volume.

Additionally or alternatively, the system and/or method can be otherwise suitably configured.

Although omitted for conciseness, the preferred embodiments include every combination and permutation of the various system components and the various method processes, wherein the method processes can be performed in any suitable order, sequentially or concurrently.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

Additional or alternative embodiments implement the above methods and/or processing modules in non-transitory computer-readable media, storing computer-readable instructions. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

As a person skilled in the art will recognize from the previous detailed description and from the figures and claims, modifications and changes can be made to the preferred embodiments of the invention without departing from the scope of this invention defined in the following claims.

We claim:

1. A system for assisted buoyant separation of target materials from a gross volume, comprising:
    a first chamber, the first chamber defined by a rigid first container;
    a second chamber, the second chamber defined by a rigid second container;
    a deformable conduit arranged between the rigid first container and the rigid second container, the deformable conduit configured to selectively fluidly connect the first and second chambers;
    a housing comprising:
        a valve configured to interface with the deformable conduit, the valve operable in a set of operation modes comprising:
            a $1^{st}$ mode, wherein in the first mode, the first chamber is fluidly disconnected from the second chamber;
            a $2^{nd}$ mode, wherein in the second mode, the first chamber is fluidly connected to the second chamber;
    an automated instrument comprising:
        a $1^{st}$ processing subsystem, wherein the housing can couple to the $1^{st}$ processing subsystem when the valve is operated in the $1^{st}$ mode, wherein the $1^{st}$ processing subsystem is configured to mix the target materials in the gross volume with a set of buoyant particles; and
        a $2^{nd}$ processing subsystem, wherein the housing can couple to the $2^{nd}$ processing subsystem when the valve is operated in the $2^{nd}$ mode, wherein the $2^{nd}$ processing subsystem is configured to separate the target materials from the gross volume with the set of buoyant particles.

2. The system of claim 1, wherein the housing is physically unable to couple with the $1^{st}$ processing subsystem when the valve is operated in the $2^{nd}$ mode.

3. The system of claim 1, wherein transitioning between the set of operation modes is achieved through relative rotation of a set of components of the valve.

4. The system of claim 3, wherein at least one of the set of components of the valve further defines a set of protruding features, wherein the relative rotation further adjusts a position of the protruding features relative to an external surface of the housing.

5. The system of claim 4, wherein the housing is physically unable to couple with the $2^{nd}$ processing subsystem when the valve is operated in the $1^{st}$ mode based on the position of the protruding features.

6. The system of claim 1, wherein mixing the target materials in the gross volume with the set of buoyant particles is performed in accordance with a mixing protocol executed by the $1^{st}$ processing subsystem, wherein the protocol prescribes a speed of rotation.

7. The system of claim 6, wherein at least one of the speed of rotation and an angle range of rotation is determined at least in part based on a volumetric amount of the gross volume.

8. The system of claim 1, wherein the valve is located exterior to an exterior wall of the deformable conduit.

9. The system of claim 8, wherein the valve comprises a set of multiple valve components that are rotatable relative to each other, wherein transitioning from the $2^{nd}$ mode to the $1^{st}$ mode comprises decreasing a diameter of an aperture defined by the set of multiple valve components through rotation, wherein the deformable conduit is arranged in the aperture.

10. The system of claim 1, wherein the target materials comprise cells, and wherein the gross volume comprises a blood volume.

11. A method for automatically assisting in buoyant separation of a set of target materials from a gross volume, comprising:
receiving, at a $1^{st}$ rigid container:
the gross volume comprising the set of target materials;
a set of buoyant particles, the set of buoyant particles configured to bind with the set of target materials;
receiving, at a $1^{st}$ processing subsystem of an automated instrument:
a housing comprising the $1^{st}$ rigid container, the housing further comprising:
a $2^{nd}$ rigid container;
a deformable conduit arranged between the $1^{st}$ rigid container and the $2^{nd}$ rigid container; and
a valve interfacing with the deformable conduit, wherein the valve selectively enables fluid communication between the $1^{st}$ rigid container and the $2^{nd}$ rigid container via the deformable conduit;
wherein the housing can be coupled with the $1^{st}$ processing subsystem only when the valve is in a closed configuration;
operating the $1^{st}$ processing subsystem, comprising mixing contents of the $1^{st}$ rigid container, thereby facilitating binding of the set of target materials with the set of buoyant particles;
receiving the housing, at a $2^{nd}$ processing subsystem of the automated instrument, wherein the housing can be coupled with the $2^{nd}$ processing subsystem only when the valve is in an open configuration; and
operating the $2^{nd}$ processing subsystem, comprising mixing contents of the $1^{st}$ and $2^{nd}$ rigid containers, thereby facilitating separation of the target material from a remainder of the gross volume.

12. The method of claim 11, wherein the $1^{st}$ and $2^{nd}$ processing subsystems are separate and distinct.

13. The method of claim 11, wherein the $1^{st}$ protocol prescribes a $1^{st}$ set of parameters, the $1^{st}$ set of parameters comprising a speed of rotation about a $1^{st}$ axis, and wherein the $2^{nd}$ protocol prescribes a $2^{nd}$ set of parameters, the $2^{nd}$ set of parameters comprising a speed of rotation about a $2^{nd}$ axis, wherein the $1^{st}$ axis is non-parallel with the $2^{nd}$ axis.

14. The method of claim 13, wherein the $1^{st}$ processing subsystem is configured for end-over-end mixing about the $1^{st}$ axis, and wherein the $2^{nd}$ processing subsystem is configured for centrifugation about the $2^{nd}$ axis.

15. The method of claim 14, wherein the centrifugation comprises swinging bucket centrifugation.

16. The method of claim 11, wherein the $1^{st}$ protocol prescribes a $1^{st}$ set of parameters, the $1^{st}$ set of parameters comprising a speed of rotation and an angle range of rotation, wherein the $1^{st}$ set of parameters is determined at least in part based on a volumetric amount of the gross volume.

17. The method of claim 11, wherein the valve is located exterior to an exterior wall of the deformable conduit.

18. The method of claim 17, wherein the valve comprises a set of multiple valve components that are rotatable relative to each other, wherein transitioning from the $2^{nd}$ mode to the $1^{st}$ mode comprises decreasing a diameter of an aperture defined by the set of multiple valve components through rotation, wherein the deformable conduit is arranged in the aperture.

19. The method of claim 17, wherein effecting the closed configuration comprises pinching the deformable conduit, thereby preventing fluid flow between the $1^{st}$ and $2^{nd}$ rigid containers.

20. The method of claim 17, wherein the open configuration enables fluid flow between the $1^{st}$ and $2^{nd}$ rigid containers.

* * * * *